(12) United States Patent
McCord et al.

(10) Patent No.: US 9,532,970 B2
(45) Date of Patent: Jan. 3, 2017

(54) COMPOSITIONS FOR ANTI-INFLAMMATORY, ANTIOXIDANT EFFECTS AND IMPROVED RESPIRATORY FUNCTION BY SPECIFIC HISTONE DEACETYLASE INHIBITION

(71) Applicants: Darlene E. McCord, Coralville, IA (US); Thomas Karagiannis, Northcote VIC (AU)

(72) Inventors: Darlene E. McCord, Coralville, IA (US); Thomas Karagiannis, Northcote VIC (AU)

( * ) Notice: Subject to any disclaimer, the term of this patent is extended or adjusted under 35 U.S.C. 154(b) by 0 days.

(21) Appl. No.: 14/793,839

(22) Filed: Jul. 8, 2015

(65) Prior Publication Data

US 2016/0008313 A1    Jan. 14, 2016

Related U.S. Application Data

(60) Provisional application No. 62/022,433, filed on Jul. 9, 2014.

(51) Int. Cl.

| | |
|---|---|
| *A61K 31/26* | (2006.01) |
| *C07C 331/20* | (2006.01) |
| *A61K 45/06* | (2006.01) |
| *A61K 31/05* | (2006.01) |
| *A61K 31/198* | (2006.01) |
| *A61K 31/7048* | (2006.01) |

(52) U.S. Cl.
CPC .............. *A61K 31/26* (2013.01); *A61K 31/05* (2013.01); *A61K 31/198* (2013.01); *A61K 31/7048* (2013.01); *A61K 45/06* (2013.01); *C07C 331/20* (2013.01)

(58) Field of Classification Search
None
See application file for complete search history.

(56) References Cited

U.S. PATENT DOCUMENTS

| | | | |
|---|---|---|---|
| 5,765,548 A | 6/1998 | Perry | |
| 8,765,794 B2 | 7/2014 | McCord | |
| 8,809,311 B2 | 8/2014 | McCord | |
| 2009/0076021 A1* | 3/2009 | Plato | A61K 31/473 514/252.14 |
| 2011/0034519 A1* | 2/2011 | McCord | A61K 31/05 514/345 |
| 2011/0245213 A1 | 10/2011 | O'Kennedy et al. | |
| 2011/0250300 A1* | 10/2011 | Biswal | A01K 67/027 424/752 |
| 2013/0116203 A1 | 5/2013 | Rajski et al. | |

FOREIGN PATENT DOCUMENTS

| | | |
|---|---|---|
| WO | 200007607 | 2/2000 |
| WO | 2004012677 | 2/2004 |

OTHER PUBLICATIONS

"Analogue" definition, Merriam-Webster OnLine Dictionary; available at http://www.merriam-webster.com/dictionary/analogue; last viewed Mar. 2010.*
Anholm, J. D. et al., J. Appl. Physiol., "Radiographic evidence of interstitial pulmonary edema after exercise at altitude", 1999, vol. 86, No. 2, pp. 503-509.*
"Derivative" definition, Merriam-Webster OnLine Dictionary; available at http://www.merriam-webster.com/dictionary/derivative; last viewed Jul. 2009.*
Morimitsu, Y. et al., The Journal of Biological Chemistry, "A Sulforaphane Analogue That Potently Activates the Nrf2-dependent Detoxication Pathway", 2002, vol. 277, No. 5, pp. 3456-3463.*
"Prevent" definition, WordNet Search—3.0; available at http://wordnet.princeton.edu; last viewed Nov. 14, 2007.*
Zhang, C. et al., Biochemical Pharmacology, "Sulforaphane enhances Nrf2 expression in prostate cancer TRAMP C1 cells through epigenetic regulation", 2013, vol. 85, pp. 1398-1404.*
Zrelli, H. et al., European Journal of Pharmacology, "Hydroxytyrosol reduces intracellular reactive oxygen species levels in vascular endothelial cells by upregulating catalase expression through the AMPK-FOXO3a pathway", 2011, vol. 660, pp. 275-285.*
Cho, Hye-Youn, "Nrf2 defends the lung from oxidative stress", Antioxidants & Redox Signaling, vol. 8, No. 1&2, 2006, 13 pages, last accessed on Sep. 1, 2015.
International Searching Authority, "International Search Report and Written Opinion", 9 pages, issued on Sep. 29, 2015.
Nian, Hui et al., "Modulation of Histone Deacetylase Activity by Dietary Isothiocyanates and Allyl Sulfides: Studies with Sulforaphane and Garlic Organosulfur Compounds", National Insitute of Health, 14 pages, issued on Apr. 30, 2009.
Cook, Robert, "Why Do Horses' Lungs Bleed?", 11 pages, date unknown.
"Dietary sulforaphane in cancer chemoprevention: The role of epigenetic regulation and HDAC inhibition", 70 pages, date unknown.

* cited by examiner

Primary Examiner — Shaojia Anna Jiang
Assistant Examiner — Bahar Craigo
(74) Attorney, Agent, or Firm — McKee, Voorhees & Sease, PLC

(57) ABSTRACT

Compositions comprising LSF compositions and treatment regiments comprising administration of LSF containing compositions are disclosed. Compositions and/or regiments may optionally include the administration of vitamins, minerals, and anti-oxidants. Methods for using these compositions and treatment regimens for treating subjects for diseases, including diseases associated with inflammation and/or oxidative stress, are provided. Various methods for use of the LSF compositions for inhibition of histone deacetylases (HDACs) in various cells, tissues, and/or conditions are also provided.

4 Claims, 18 Drawing Sheets

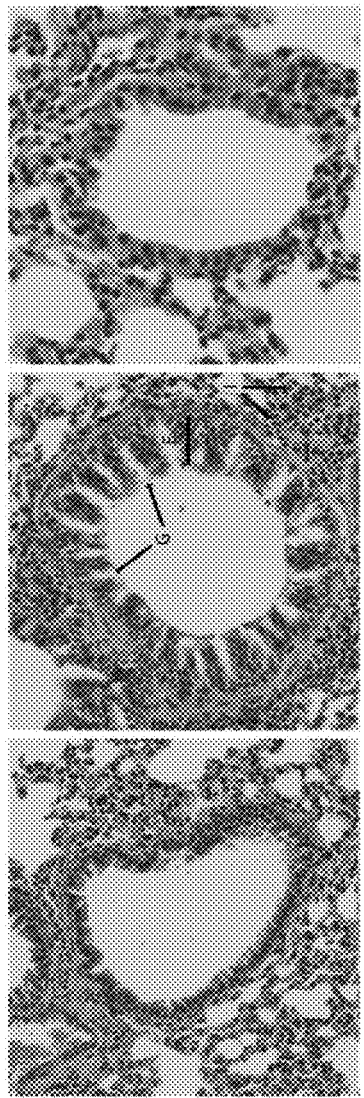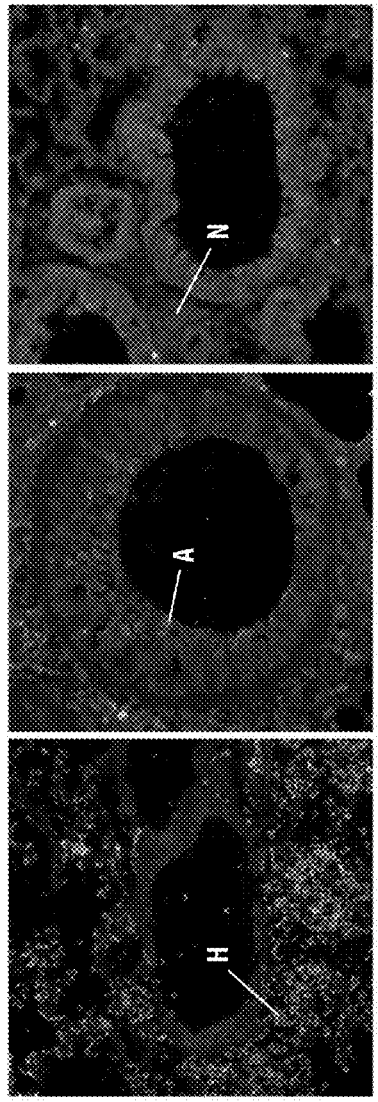
FIG. 4A  FIG. 4B  FIG. 4C
saline (control)  ovalbumin-vehicle  ovalbumin-L-sulforaphane
E = airway epithelial thickening
G = goblet cell hyperplasia
I = marked inflamation
FIG. 4D  FIG. 4E  FIG. 4F
A = Annexin V (apoptosis)
N = DAPI (nucleus)
H = HDAC8 (histone)

COMPOSITIONS FOR ANTI-INFLAMMATORY, ANTIOXIDANT EFFECTS AND IMPROVED RESPIRATORY FUNCTION BY SPECIFIC HISTONE DEACETYLASE INHIBITION

CROSS-REFERENCE TO RELATED APPLICATIONS

This application claims priority to Provisional Application U.S. Ser. No. 62/022,433 filed on Jul. 9, 2014, which is herein incorporated by reference in its entirety.

FIELD OF THE INVENTION

The invention relates to compositions comprising L-sulforaphane (LSF) and to treatment regiments comprising L-sulforaphane (LSF) compositions. Compositions and/or regiments may optionally include the administration of vitamins, minerals, and/or anti-oxidants. Methods for using these compositions and treatment regimens for treating subjects for diseases and conditions related to inflammation and/or oxidative stress, such as pulmonary edema and exercise-induced pulmonary hemorrhage, are provided. The invention further relates to various methods for use of the LSF compositions for inhibition of histone deacetylases.

BACKGROUND OF THE INVENTION

Pulmonary edema is a condition caused by excess fluid in the lungs. This fluid collects in the numerous air sacs in the lungs, making it difficult to breathe. The most common cause of pulmonary edema is heart problems, but fluid can accumulate for other reasons, including pneumonia, exposure to certain toxins and medications, and exercising or living at high elevations.

Pulmonary edema that develops suddenly (acute) is a medical emergency requiring immediate care, and can sometimes prove fatal. Treatment for pulmonary edema varies depending on the cause, but generally includes supplemental oxygen and medications, and may require both acute treatments along with ambulatory treatment for the underlying problem.

Oxidative stress and inflammatory responses are key features of pulmonary edema and exercise-induced pulmonary hemorrhage (EIPH). Neutrophils and hemosiderophages (macrophages that have ingested and digested red blood cells) are present in high numbers in the lungs of animals suffering from EIPH, indicating an influx of inflammatory cells. Similarly, hypoxia has been highly implicated Pulmonary edema is of particular concern in elite athletes. For example, EIPH is an endemic production disease form of pulmonary edema of racing and other high-intensity exercise horses, which occurs when blood enters the air passages of a horse's lung, which may lead to the impairment of lung function. EIPH or "bleeding" has been a recognized condition in racing horses for at least three hundred years, and has been reported to occur in a variety of race horse breeds including racing Thoroughbreds (both flat racing and steeple chasing or jump racing), American Quarter Horses (incidence of 50-75%), Standardbreds (incidence of 40-60%), Arabians, and Appaloosas. EIPH has also been reported in eventers, jumpers, polo ponies, endurance horses, draft horses that pull competitively, and horses taking part in Western speed events such as reining, cutting and barrel racing. Virtually all horses that are subjected to intense exercise bleed into the lungs, and these episodes of bleeding often commence as soon as these horses enter training, making EIPH a major welfare and economic concern to both veterinarians, and those involved in the racing and sport horse industries. Healing occurs, but complete restoration of pulmonary function in the affected area often does not occur. Repeated episodes of intense exercise can result in repeated episodes of pulmonary hemorrhage, and cumulative damage to the affected lung tissue can occur such as e.g., fibrosis and/or scaring and consolidation of alveoli. These chronic changes occur, particularly in the dorsocaudal lobes of the lung, and such changes can eventually curtail the performance of the horse.

Preventative/ameliorative/curative/restorative measures for EIPH affected horses have also been sought for several hundred years. For many years, the treatment of choice for prevention of EIPH in the race horse has been pre-race treatment with the diuretic furosamide (Lasix®). However, the exact mechanism of action of furosamide in prevention of EIPH is unknown, although many theories have been postulated over the years, its effectiveness is in question, and its use in racing is illegal in all countries with the exceptions of the U.S. and Canada. The treatment of choice for EIPH, after the fact, is usually rest (mandatory in many racing jurisdictions) and often in conjunction with antibiotics to prevent secondary bacterial infection and/or the use of anti-inflammatory medication.

More recently, (following the research of West et al. J. Appl. Physiol. 1993, 75: 1097-1109 related to the relationship of EIPH and increased pulmonary artery pressure) attempts at treating EIPH via nitric oxide administration have been tried, e.g., by Perry (U.S. Pat. No. 5,765,548). Perry describes administration of nitric oxide through continuous insufflation of the nitric oxide to the horse during the exercise period. Alternatively, the horse is treated with insufflation of nitric oxide prior to the exercise event and then is given an intramuscular injection of a phosphodiesterase inhibitor, e.g., ZAPRINAST. The treatment during exercise as described by Perry is both cumbersome and problematic for the racing animal and has never gained widespread acceptance. Likewise, systemic treatment of the racing animal with phosphodiesterase inhibitors opens the door for unwanted side effects and requires regulatory scrutiny.

Histone deacetylases (HDACs) are a class of enzymes that remove acetyl groups (O=C≤CH3) from an ϵ-N-acetyl lysine amino acid on a histone, allowing the histones to wrap the DNA more tightly. Together with the acetylpolyamine amidohydrolases and the acetoin utilization proteins, the histone deacetylases form an ancient protein superfamily known as the histone deacetylase superfamily. HDACs are classified in four classes depending on sequence homology to the yeast original enzymes and domain organization. The Class I HDACs are HDAC1, HDAC2, HDAC3, and HDAC8. The Class IIA HDACs are HDAC4, HDAC5, HDAC7, and HDAC9. The Class IIB HDACs are HDAC6 and HDAC10. Class III HDACs include the sirtuin proteins (SIRT1-7). The HDAC11 is the Class IV HDAC. HDACs in Classes I, II, and IV (HDACs1-11) are metal-dependant HDACs. By modulating the acetylation status of histones, histone deacetylase inhibitors alter the transcription of genes involved in cell growth, maturation, survival and apoptosis, among other processes. In addition to histones, HDACs have many non-histone protein substrates which have a role in regulation of gene expression, cell proliferation, cell migration, cell death, and angiogenesis.

The organosulfur compound L-sulforaphane (LSF) is obtained from cruciferous vegetables (such as broccoli, Brussels sprouts or cabbages) when hydrolytic conversion of glucoraphanin to sulforaphane through the action of physical damage to the plant occurs either by the action of plant-derived myrosinase (intracellular broccoli thioglucosidase), or by the microbiota of the human colon. Approximately, 60-80% of glucoraphanin is converted to sulforaphane, with most broccoli varieties possessing between 0.1 and 30 µmol/g of glucoraphanin.

LSF is known to have potent antioxidant effects by activation of the Nrf2-ARE detoxification pathway. Nrf2 is a CNC (cap 'n' collar) bZIP (basic region leucine zipper) group of transcription factors which is broadly expressed in a variety of tissues. Quiescent Nrf2 localizes in the cytoplasm and is rapidly turned over through a specific ubiquitin-26S proteasome pathway controlled by the Keap1/Cul3-independent ubiquitin ligase (E3). Nrf2 is activated in response to a range of oxidative and electrophilic stimuli including ROS, heavy metals and certain disease processes. Upon activation, Nrf2 mediates antioxidant response by the induction of a broad range of genes including phase 2 enzymes, such as NAD(P)H:quinone oxidoreductase 1 (NQO1) and heme oxygenase-1, and antioxidant proteins, such as SOD and catalase. Both genetic and biochemical studies have implicated the Nrf2 signaling pathway in the defense against a wide range of chemical toxicity, cancer and chronic diseases in which oxidative stress is involved. LSF has been shown to protect against oxidative stress and apoptosis by the induction of Nrf2-mediated antioxidant response.

Therefore, it is a primary object, feature, or advantage of the present invention to improve upon the state of the art.

It is a further object, feature, or advantage of the present invention to provide methods of treating and/or preventing diseases associated with inflammation. In one aspect, the methods of treating and/or preventing diseases associated with inflammation involve providing or administering an effective amount of L-sulforaphane to a subject in need thereof. The L-sulforaphane may be combined with other components, including, for example, antioxidant or anti-inflammatory compounds. In a particular embodiment, L-sulforaphane can be administered or provided in combination with one or more of hydroxytyrosol, oleuropein, N-acetylcysteine, L-proline, glycine, and taurine.

It is a further objective, feature or advantage of the present invention to provide methods of treating and/or preventing pulmonary edema, including for example EIPH. In one aspect, the methods of treating and/or preventing pulmonary edema involve providing or administering an effective amount of L-sulforaphane to a subject in need thereof. The L-sulforaphane may be combined with other components, including, for example, antioxidant or anti-inflammatory compounds. In one embodiment, the methods involve providing or administering a nasal spray.

It is a further objective, feature or advantage of the present invention to provide compositions and methods for inhibiting HDACs. In one aspect the compositions and methods provide specific inhibition of Class I HDACs, and in particular embodiments specific inhibition of HDAC8.

It is a further objective, feature or advantage of the present invention to provide compositions and methods for altering gene expression in a cell, tissue, or subject, including by increasing lysine acetylation, and/or increasing or decreasing gene expression in cells or tissues contacted with an LSF containing composition. These methods may be used for improving cell viability and/or treating or preventing oxidative stress in an individual or cell.

BRIEF SUMMARY OF THE INVENTION

The present invention provides compositions and methods for treating or preventing pulmonary edema, including exercise-induced pulmonary hemorrhage (EIPH). In one aspect, the invention encompasses compositions and methods comprising L-sulforaphane (LSF) for treating or preventing pulmonary edema. LSF may be combined with other components, vitamins, minerals, and anti-oxidants, including one or more of hydroxytyrosol, oleuropein, N-acetylcysteine, L-proline, glycine, and taurine.

In another aspect, the invention provides methods of treating or preventing conditions or diseases associated with inflammation or oxidative stress, comprising administering to a subject in need thereof a composition comprising LSF, an LSF derived and/or substituted compound, and/or an LSF analogue. In a preferred embodiment, the disease or condition is pulmonary edema or EIPH. In a more preferred embodiment, the subject is a human athlete or a horse.

In another aspect, the invention provides methods of inhibiting one or more histone deacetylases (HDAC) in a cell comprising contacting said cell with a composition comprising L-sulforaphane (LSF), an LSF derived and/or substituted compound, and/or an LSF analogue. In a preferred embodiment, the HDAC is a Class I HDAC. In a more preferred embodiment the HDAC is HDAC8.

In another aspect, the invention provides method for increasing or decreasing gene expression in a cell, tissue, or subject, including by increasing lysine acetylation of a histone polypeptide, using a composition comprising L-sulforaphane (LSF), an LSF derived and/or substituted compound, and/or an LSF analogue. In a more particular aspect, the genes may be involved in type I (alpha/beta) and type II (gamma) interferon (IFN) signaling. In another aspect increasing or decreasing of gene expression can be one or more of upregulation of general transcription factors (POL2, TAF1) and downregulation of STAT1, STAT2 and RAD21 targets.

In another aspect, the invention provides methods for improving cell viability and/or treating or preventing oxidative stress in an individual or cell, comprising contacting said cell with a with a composition comprising L-sulforaphane (LSF), an LSF derived and/or substituted compound, and/or an LSF analogue.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
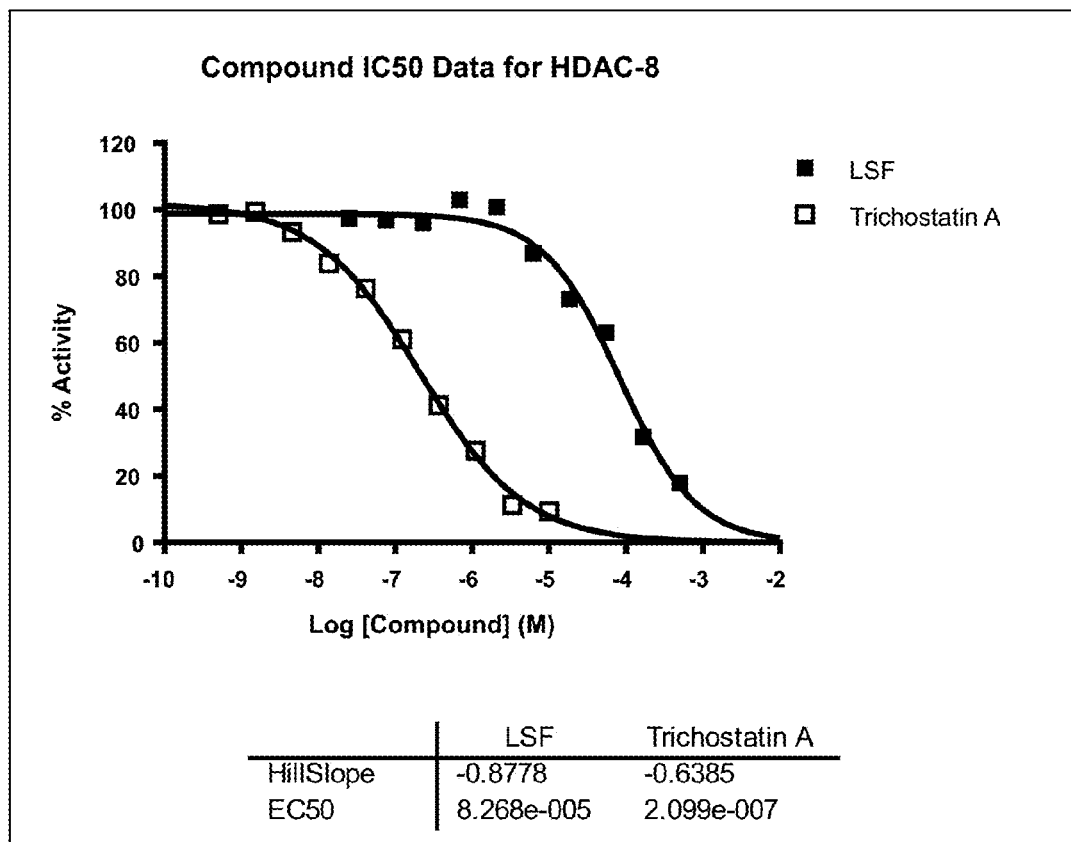
FIG. 1 shows binding of L-sulforaphane to histone deacetylase 8 relative to the prototypical histone deacetylase inhibitor, Trichostatin A.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE PREFERRED EMBODIMENT

The embodiments of this invention are not limited to particular compositions and methods of use thereof, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form. Numeric ranges recited within the specification are inclusive of the numbers defining the range and include each integer within the defined range.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

In the present invention, an "effective amount" or "therapeutically effective amount" of a compound or of a composition of the present invention is that amount of such compound and/or composition that is sufficient to affect beneficial or desired results as described herein. In terms of treatment of a mammal, e.g., a human patient, an "effective amount" is an amount sufficient to at least slow the progression or spread of disease, or render the disease susceptible to therapeutics or remediation.

The efficacy of the compositions in treating or preventing a particular disease, disorder, or condition according to the present invention can be evaluated both in vitro and in vivo. As used herein, the term "treating" refers to: (i) preventing a disease, disorder or condition from occurring in a mammal, animal or human that may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition. For example, the compositions of the present invention may be used to prevent EIPH from occurring in racing horses (i.e. prior to exercise), to arrest the development of EIPH in racing horses (i.e. during exercise), and/or to relieve EIPH in horses (i.e. after exercise). The efficacy of such compositions treatment may be measured quantitatively or qualitatively to determine the presence/absence of the disease, or its progression or regression using, in the example of EIPH, reduction in blood in the lungs, a reduction in inflammatory infiltration, a reduction or absence of other symptoms of EIPH, and/or no worsening in disease over a specified period of time or other symptoms associated with the disease or clinical indications associated with the pathology of cancer development. In one aspect, this treatment may be accomplished by administering the compositions to a subject in need thereof, for example by providing a nasal spray.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

As one skilled in the art shall appreciate, there are two distinct mechanisms for cell death. Apoptosis is the result of "normal" or programmed cell death. Through this physiological process cells are routinely eliminated, giving balance to the proliferation of new cells. During apoptosis the outer membrane of the cell forms "bubbles" known as blebs. The content of the cells becomes incased in the blebs. The blebs separate from the cell and are digested by nearby cells or macrophages. This orderly process greatly reduces toxicity to surrounding cells.

Inflammation refers to the process by which an organism attempts to remove injurious stimuli and to initiate the healing process, classically indicated by pain, heat, redness, swelling, and/or loss of function. Inflammation may be either acute (the initial response of the body to harmful stimuli primarily involving increased movement of plasma and leukocytes from the blood into the injured tissues) or chronic. The inflammatory response involves a cascade of biochemical events, implicating local vascular systems, the immune system, and various cells within the injured tissue. Inflammation may be detected or measured, for example, by the presence of inflammatory cells, including white blood cells such as neutrophils, monocytes/macrophages, B-cells, T-cells, NK-cells; myeloperoxidase (MPO) activity; and/or the presence of inflammatory mediators, including cytokines and chemokines such as TNF-α, IL-1l3, IL-6, IL-8, MIP-1l3 and IP-10.

The methods and compositions of the present invention may comprise, consist essentially of, or consist of the components and ingredients of the present invention as well as other ingredients described herein. As used herein, "consisting essentially of" means that the methods and compositions may include additional steps, components or ingredients, but only if the additional steps, components or ingredients do not materially alter the basic and novel characteristics of the claimed methods and compositions.

Compositions

In an aspect of the invention the administration of LSF results in prevention or treatment of inflammation and/or oxidative stress. In one embodiment, administration of LSF results in the prevention or treatment of pulmonary edema, including for example EIPH. According to the invention, the selective effects of LSF administration is mediated by specific inhibition of histone deacetylases (HDACs), including HDAC8. In an aspect, the LSF compositions are employed as a pre-treatment for subjects that may develop pulmonary edema or EIPH, including human athletes, individuals that will be at high altitude (elevation >2,500 meters), and racing horses. The compositions according to the invention provide a biochemical mechanism by which cellular and/or systemic characteristics are regulated. The compositions and/or treatment regimens according to the invention include LSF, and may include one or more of hydroxytyrosol, oleuropein, N-acetylcysteine, L-proline, glycine, and taurine.

As referred to herein, LSF compositions include any LSF-based inhibitor of HDAC proteins. Suitable LSF-based inhibitor of the HDAC proteins include, for example, LSF, a LSF derived compound, a LSF substituted compound, a LSF metabolite (originating from a prodrug), and combinations of the same. A LSF composition may further include a carrier, diluent and/or other pharmaceutically acceptable delivery agents or the like.

L-Sulforaphane

The compositions according to the invention employ L-sulforaphane (LSF). L-sulforaphane (LSF; CAS Registry number [CAS 142825-10-3]), is also known as (R)-1-Isothiocyanato-4-(methylsulfinyl)butane, 4-Methylsulfinylbutyl isothiocyanate. LSF has the structure set out below:

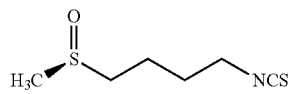

For use in the composition of the present invention, LSF may be derived from natural sources or prepared by chemical synthesis. For example, the LSF may be obtained as an extract of, or otherwise derived from, seeds, leaves, fruits, or other parts of cruciferous vegetables, and/or vegetation water of cruciferous vegetable production.

In addition to isolated, purified, derived and/or synthesized LSF compositions, according to a further embodiment, a LSF derivative and/or substituted LSF, include for example sulforaphane-glutathione conjugate derivatives according to the following structure:

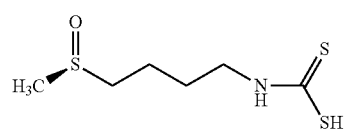

In addition, analogues of LSF can be employed for compositions and methods of the present invention. Analogues may include compounds with the following general formula:

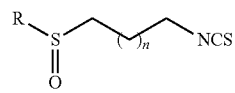

Such analogues are understood to include any such compound wherein R provides a pharmaceutically acceptable salt, solvate, prodrug and/or isomer of LSF having the desired beneficial effect of treating or preventing pulmonary edema, including EIPH. Such analogues can include, for example, 6-(Methylsulfinyl)hexyl isothiocyanate, D, L-sulforaphane, and (±)-4-methylsulfinyl-1-(S-methyldithiocarbamyl)-butane.

In a further embodiment, compounds derived from LSF (LSF derivatives), LSF substituted compounds, metabolites of LSF (its derivatives and/or substituted compounds), one or more mixtures thereof, or one or more combinations thereof are employed for LSF compositions.

The term "prodrug" as understood by one skilled in the art refers to compounds or derivatives that are converted in vivo to the compounds of the invention as a result of spontaneous chemical reaction(s), enzyme catalyzed chemical reaction(s), and/or metabolic chemical reaction(s). Examples of prodrugs include, but are not limited to, derivatives and metabolites of the compounds of the formula set forth according to the present invention. These may include, for example, biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Further, prodrugs include compounds that can be oxidized, reduced, aminated, deaminated, esterified, deesterified, alkylated, dealkylated, acylated, deacylated, phosphorylated, dephosphorylated, or other functional group change or conversion involving forming or breaking chemical bonds on the prodrug, by either enzymatic action or by general acid or base solvolysis. Prodrugs can be prepared according to methods known to one skilled in the art, such as those described by Burger "Medicinal Chemistry and Drug Discovery 6th ed. (Donald J. Abraham ed., 2001, Wiley) and "Design and Applications of Prodrugs" (H. Bundgaard ed., 1985, Harwood Academic Publishers). Without limiting the scope of the invention, any compound that is a prodrug of a compound of the formulas according to the invention are included within the scope of the invention.

In a still further embodiment, LSF derivatives, substituted LSF and/or LSF analogues, including for example LSF acyl derivatives, substituted hydroxyl groups and/or substituted compositions, are employed and have the following general structure:

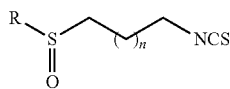

wherein R is selected from the group consisting of hydrogen, substituted or unsubstituted alkyl, substituted or unsubstituted alkenyl, substituted or unsubstituted alkynyl, substituted or unsubstituted aryl, substituted or unsubstituted heterocyclyl, substituted or unsubstituted acyl, ORa, SRa, SORa, SO2Ra, OSO2Ra, OSO3Ra, NO2, NHRa, N(Ra)2, =N—Ra, N(Ra)CORa, N(CORa)2, N(Ra)SO2R', N(Ra)C(=NRa)N(Ra)Ra, CN, halogen, CORa, COORa, OCORa, OCOORa, OCONHRa, OCON(Ra)2, CONHRa, CON(Ra)2, CON(Ra)ORa, CON(Ra)SO2Ra, PO(ORa)2, PO(ORa)Ra, PO(ORa)(N(Ra)Ra) and aminoacid ester having inhibitory efficacy against HDAC8 protein; and further wherein the R group is selected from the group consisting of hydrogen, substituted or unsubstituted alkyl, substituted or unsubstituted alkenyl, substituted or unsubstituted alkynyl, substituted or unsubstituted aryl, and substituted or unsubstituted heterocyclyl, substituted or unsubstituted acyl, and the like having inhibitory efficacy against HDAC8 protein; and further wherein each of the substituted or unsubstituted alkyl, alkenyl, alkynyl, aryl, heterocyclyl, and/or acyl groups are C1-28 (including all ranges therein).

"Alkyl" refers to a straight or branched hydrocarbon chain radical consisting of carbon and hydrogen atoms, containing no unsaturation, and which is attached to the rest of the molecule by a single bond. Alkyl groups may include straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups). Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

Alkyl groups preferably have from 1 to about 22 carbon atoms. Methyl, ethyl, n-propyl, iso-propyl and butyl, including n-butyl, tert-butyl, sec-butyl and iso-butyl are particularly preferred alkyl groups. As used herein, the term alkyl, unless otherwise stated, refers to both cyclic and noncyclic groups, although cyclic groups will comprise at least three carbon ring members, such as cyclopropyl or cyclohexyl. Alkyl radicals may be optionally substituted by one or more substituents, such as an aryl group, like in benzyl or phenethyl.

"Alkenyl" and "Alkynyl" refer to a straight or branched hydrocarbon chain radical consisting of carbon and hydrogen atoms, containing at least one unsaturation (one carbon-carbon double or triple bond respectively) and which is attached to the rest of the molecule by a single bond. Alkenyl and alkynyl groups preferably have from 2 to about 22 carbon atoms. The terms alkenyl and alkynyl as used herein refer to both cyclic and noncyclic groups, although cyclic groups will comprise at least three carbon ring members. Alkenyl and alkenyl radicals may be optionally substituted by one or more substituents.

"Aryl" refers to a radical derived from an aromatic hydrocarbon by removal of a hydrogen atom from a ring carbon atom. Suitable aryl groups in the present invention include single and multiple ring compounds, including multiple ring compounds that contain separate and/or fused aryl groups. Typical aryl groups contain from 1 to 3 separated and/or fused rings and from 6 to about 22 carbon ring atoms. Aryl radicals may be optionally substituted by one or more substituents. Specially preferred aryl groups include substituted or unsubstituted phenyl, substituted or unsubstituted naphthyl, substituted or unsubstituted biphenyl, substituted or unsubstituted phenanthryl and substituted or unsubstituted anthryl.

"Heterocyclyl" refers to a cyclic radical having as ring members atoms of at least two different elements. Suitable heterocyclyl radicals include heteroaromatic and heteroalicyclic groups containing from 1 to 3 separated and/or fused rings and from 5 to about 18 ring atoms. Preferably heteroaromatic and heteroalicyclic groups contain from 5 to about 10 ring atoms. Heterocycles are described in: Katritzky, Alan R., Rees, C. W., and Scriven, E. Comprehensive Heterocyclic Chemistry (1996) Pergamon Press; Paquette, Leo A.; Principles of Modern Heterocyclic Chemistry W. A. Benjamin, New York, (1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28. Suitable heteroaromatic groups in the compounds of the present invention contain one, two or three heteroatoms selected from N, O or S atoms and include, e.g., coumarinyl including 8-coumarinyl, quinolyl including 8-quinolyl, isoquinolyl, pyridyl, pyrazinyl, pyrazolyl, pyrimidinyl, furyl, pyrrolyl, thienyl, thiazolyl, isothiazolyl, triazolyl, tetrazolyl, isoxazolyl, oxazolyl, imidazolyl, indolyl, isoindolyl, indazolyl, indolizinyl, phthalazinyl, pteridinyl, purinyl, oxadiazolyl, thiadiazolyl, furazanyl, pyridazinyl, triazinyl, cinnolinyl, benzimidazolyl, benzofuranyl, benzofurazanyl, benzothienyl, benzothiazolyl, benzoxazolyl, quinazolinyl, quinoxalinyl, naphthyridinyl, and furopyridinyl. Suitable heteroalicyclic groups in the compounds of the present invention contain one, two or three heteroatoms selected from N, O or S atoms and include, e.g., pyrrolidinyl, tetrahydrofuryl, dihydrofuryl, tetrahydrothienyl, tetrahydrothiopyranyl, piperidyl, morpholinyl, thiomorpholinyl, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, pyrazolidinyl, imidazolinyl, imidazolidinyl, 3-azabicyclo[3.1.0]hexyl, 3-azabicyclo[4.1.0]heptyl, 3H-indolyl, and quinolizinyl. Heterocylic radicals may be optionally substituted by one or more substituents.

In each of the aforementioned embodiments, the components of the composition of the present invention may optionally be present in the form of an ester or a physiologically and/or pharmaceutically acceptable salt. Exemplary pharmaceutically acceptable salts refers to salts prepared from pharmaceutically acceptable non-toxic acids, including inorganic salts and organic salts. Suitable non-organic salts include inorganic and organic acids such as acetic, benzenesulfonic, benzoic, camphorsulfonic, citric, ethenesulfonic, fumaric, gluconic, glutamic, hydrobromic, hydrochloric, isethionic, lactic, malic, maleic, mandelic, methanesulfonic, mucic, nitric, pamoic, pantothenic, phosphoric, succinic, sulfuric, tartaric acid, p-toluenesulfonic and other pharmaceutically acceptable salts as provided in Stahl and Wermuth "Pharmaceutical Salts Properties, Selection, and Use", 1st Ed, Wiley-VCH, 374 (2002).

In an aspect, the compositions according to the invention deliver at least about 1 µM LSF, at least about 5 µM LSF, at least about 10 µM LSF, at least about 20 µM LSF, at least about 50 µM LSF, at least about 100 µM LSF, or greater. In general, larger doses tend to produce greater effects, with the preferred dosage also depending, at least in part, upon weight, metabolism, individual body chemistry, type of cancer or other condition being treated, and the like.

In an embodiment the dose of LSF administered to a person is about 0.01 micrograms per kilogram of body weight to about 100 milligrams per kilogram of body weight. In addition, without being limited according to the invention, all ranges recited are inclusive of the numbers defining the range and include each integer within the defined range. In a further aspect, the LSF is present at a level such that an effective amount for the reduction of inflammation and/or oxidative stress in the target cells or tissues results.

Depending upon the route of administration, greater doses of LSF may be administered. For example, significantly lesser amounts of LSF may be absorbed when the route of administration is inhaled (i.e. aerosol or spray) as compared to parenteral or other forms of systemic administration. For inhaled delivery, therefore, the daily dose of LSF administered by inhalation may be about 0.01 micrograms to about 1000 micrograms per kilogram of body weight. By way of further example, in one embodiment, the daily dose of LSF administered to a subject by inhalation is about 1 to about 100 micrograms per kilogram of body weight. By way of further example, in one embodiment, the daily dose of LSF administered to a subject by inhalation is about 5 to about 50 micrograms per kilogram of body weight. By way of further example, in one embodiment, the daily dose of LSF administered to a subject by inhalation is about 10 micrograms to about 50 micrograms per kilogram of body weight.

For parenteral delivery the daily dose may be from about 0.01 to about 100 micrograms per kilogram of body weight per day, twice a day, or more than twice a day. In one embodiment, the daily dose of LSF parenterally administered to a person is about 0.1 to about 50 micrograms per kilogram of body weight per day. In another such embodiment, the daily dose of LSF parenterally administered to a person is about 0.1 to about 10 microgram per kilogram of body weight.

Regardless of the route of administration of the LSF, the compositions may be administered in a single dose or multiple doses to achieve a target daily dose. For example, for certain embodiments the LSF is provided in a formulation that will provide a single daily dose. Alternatively, for such embodiments the LSF is provided in a formulation that will provide, in two or more doses over the course of a day.

As one skilled in the art appreciates, greater amounts of LSF may be included in the dosage unit form when the intended route of administration is oral. For example, typical dosage forms for oral administration include tablets, pills, capsules, gelcaps, caplets, and the like. A single dose, therefore, may comprise a single tablet, pill, capsule, gelcap, caplet or the like, or two or more tablets, pills, capsules, gelcaps, caplets, and the like. In general, dosage forms for oral administration may contain 0.01 to 100 milligrams of LSF. For example, in one embodiment, the dosage unit form contains 1 to 50 milligrams LSF.

The route of administration may affect the rate and extent of absorption of LSF. Taking this into account, i.e., taking into account the fraction of an administered dose that is not absorbed or for whatever reason is not systemically bioavailable to the subject, it is generally preferred that the administered dose provide the subject with at least about 100 but less than about 10,000, preferably less than about 6,000 TE of systemically bioavailable LSF per day. In general, it is preferred that the administered dose provide the subject with at least about 250 TE of systemically bioavailable LSF per day. In certain embodiments, it is preferred that the administered dose provide the subject with at least about 500, at least about 750, at least about 1,000, or at least about 5,000 TE of systemically bioavailable LSF per day.

Additional Functional Ingredients

The components of the treatment compositions according to the invention can further be combined with various functional components suitable for use treating the particular cancer or other condition. Additional functional ingredient components may include those that improve the health and/or viability of a patient and/or the cells of a patient.

In other embodiments, additional functional ingredients may be included in the compositions. The functional ingredients provide desired properties and functionalities to the compositions. For the purpose of this application, the term "functional ingredient" includes a material that when combined with the LSF provides a beneficial property in a particular use or treatment. Some particular examples of functional materials are discussed in more detail below, although the particular materials discussed are given by way of example only, and that a broad variety of other functional ingredients may be used.

In some embodiments, the compositions may include additional components, such as those that improves the health or viability of cells. In some aspects, such additional functional ingredients may include, for example hydroxytyrosol, oleuropein, N-acetylcysteine, antioxidants, vitamins, minerals, and/or additional components. Such additional components, for example, may include other antioxidants, vitamins, minerals, and/or amino acids. Non-limiting examples of other antioxidants include ascorbic acid (vitamin C) and its salts, ascorbyl esters of fatty acids, ascorbic acid derivatives (e.g., magnesium ascorbyl phosphate, sodium ascrobyl phosphate, and ascorbyl sorbate), EGCG, oleuropein, tocopherol (vitamin E), tocopherol sorbate, tocopherol acetate, other esters of tocopherol, tyrosol, butylated hydroxy benzoic acids and their salts, gallic acid and its alkyl esters such as propyl gallate, uric acid and its salts and alkyl esters, sorbic acid and its salts, lipoic acid, amines (e.g., N,N-diethylhydroxylamine and amino-guanidine), sulfhydryl compounds (e.g., glutathione), dihydroxy fumaric acid and it salts, glycine pidolate, arginine pilolate, nordihydroguaiaretic acid, bioflavinoids, curcumin, lysine, methionine, proline, superoxide dismutase, resveratrol, and other polyphenols. In another embodiment, the composition comprises hydroxytyrosol, N-acetylcysteine, and one or more of cystine, cystine derivatives, vitamin C, tannic acid, vitamin E, vitamin E derivatives, catechin, niacin, unsaturated fatty acids, vitamin P, vitamin Q, glutathione, isoflavones, guava, selenium, oleuropein or other polyphenol(s). In one embodiment, the composition comprises hydroxytyrosol, N-acetylcysteine and one or more of glycine, L-taurine, L-proline, niacinamide (vitamin B3), pyridoxine (vitamin B6), and methylsulfonylmethane.

In one embodiment, the composition contains non-amino acid additives such as aloe vera, oat extract, hyaluronic acid, betaglucan or like substance to provide glycosaminoglycans for extracellular matrix protection. Vitamins may be additives, especially vitamins A/D3, all B vitamins and all stable C vitamins. Omega 3 and 6 fatty acids will be balanced with the greater percentage being 3. In one embodiment, the composition may contain other antioxidants, anti-inflammatory agents and tissue repair ingredients known to have wound healing benefits. For example, in one embodiment, the composition contains olive leaf extract, vitamin A/D3, Vitamin C, and essential fatty acids from olive oil, canola oil, safflower oil, borrage oil and sunflower oil. Also preferably, olive leaf extract is present in the composition of the present invention.

In one embodiment, the compositions include one or more of LSF, hydroxytyrosol, oleuropein, N-acetylcysteine, L-proline, glycine, and taurine. In one embodiment, the composition contains N-acetylcysteine and hydroxytyrosol and the weight ratio of N-acetylcysteine to hydroxytyrosol to between 1:1 and 50:1, respectively. In one embodiment, the composition contains N-acetylcysteine and hydroxytyrosol and the weight ratio of N-acetylcysteine to hydroxytyrosol is between 10:1. and 30:1, respectively. For example, in one such embodiment, the composition contains N-acetylcysteine and hydroxytyrosol and the weight ratio of N-acetylcysteine to hydroxytyrosol is between 20:1 and 25:1, respectively.

In one embodiment, the composition contains glycine and hydroxytyrosol and the weight ratio of glycine to hydroxytyrosol to between 1:1 and 50:1, respectively. In one embodiment, the composition contains glycine and hydroxytyrosol and the weight ratio of glycine to hydroxytyrosol is between 30:1 and 40:1, respectively. For example, in one such embodiment, the composition contains glycine and hydroxytyrosol and the weight ratio of glycine to hydroxytyrosol is about 35:1, respectively.

In one embodiment, the composition contains L-taurine and hydroxytyrosol and the weight ratio of L-taurine to hydroxytyrosol to between 1:1 and 50:1, respectively. In one embodiment, the composition contains L-taurine and hydroxytyrosol and the weight ratio of L-taurine to hydroxytyrosol is between 20:1 and 50:1, respectively. In one embodiment, the composition contains L-taurine and hydroxytyrosol and the weight ratio of L-taurine to hydroxytyrosol is between 30:1 and 40:1, respectively. For example, in one such embodiment, the composition contains L-taurine and hydroxytyrosol and the weight ratio of L-taurine to hydroxytyrosol is about 35:1, respectively.

In one embodiment, the composition contains L-proline and hydroxytyrosol and the weight ratio of L-proline to hydroxytyrosol to between 1:1 and 20:1, respectively. In one embodiment, the composition contains L-proline and hydroxytyrosol and the weight ratio of L-proline to hydroxytyrosol is between 1:1 and 10:1, respectively. In one embodiment, the composition contains L-proline and hydroxytyrosol and the weight ratio of L-proline to hydroxytyrosol is between 1:1 and 5:1, respectively.

In one embodiment, the composition contains methylsulfonylmethane and hydroxytyrosol and the weight ratio of methylsulfonylmethane to hydroxytyrosol to between 1:1 and 30:1, respectively. In one embodiment, the composition contains methylsulfonylmethane and hydroxytyrosol and the weight ratio of methylsulfonylmethane to hydroxytyrosol is between 5:1 and 25:1, respectively. In one embodiment, the composition contains methylsulfonylmethane and hydroxytyrosol and the weight ratio of methylsulfonylmethane to hydroxytyrosol is between 10:1 and 20:1, respectively.

In one embodiment, the composition contains niacinamide and hydroxytyrosol and the weight ratio of niacinamide to hydroxytyrosol to between 1:1 and 10:1, respectively. In one embodiment, the composition contains niacinamide and hydroxytyrosol and the weight ratio of niacinamide to hydroxytyrosol is between 1:1 and 5:1, respectively. In one embodiment, the composition contains niacinamide and hydroxytyrosol and the weight ratio of niacinamide to hydroxytyrosol is between 1:1 and 2:1, respectively.

In one embodiment, the composition contains pyridoxine and hydroxytyrosol and the weight ratio of pyridoxine to hydroxytyrosol to between 1:1 and 10:1, respectively. In one embodiment, the composition contains pyridoxine and hydroxytyrosol and the weight ratio of pyridoxine to hydroxytyrosol is between 1:1 and 5:1, respectively. In one embodiment, the composition contains pyridoxine and hydroxytyrosol and the weight ratio of pyridoxine to hydroxytyrosol is between 1:1 and 2:1, respectively.

In one preferred embodiment, the composition of the present invention contains hydroxytyrosol, N-acetylcysteine and optionally one or more of glycine, L-taurine, L-proline, niacinamide (B3), pyridoxine (B6), and methylsulfonylmethane. In one example of this embodiment, the weight ratio N-acetylcysteine to hydroxytyrosol is between 1:1 and 50:1, respectively, the weight ratio glycine to hydroxytyrosol is between 1:1 and 50:1, respectively, the weight ratio of L-taurine to hydroxytyrosol is between 1:1 and 50:1, respectively, the weight ratio of L-proline to hydroxytyrosol is between 1:1 and 20:1, respectively, the weight ratio of niacinamide to hydroxytyrosol is between 1:1 and 10:1, respectively, the weight ratio of pyridoxine to hydroxytyrosol is between 1:1 and 10:1, and the weight ratio of methylsulfonylmethane to hydroxytyrosol is between 1:1 and 30:1. In another example of this embodiment, the weight ratio N-acetylcysteine to hydroxytyrosol is between 10:1 and 30:1, respectively, the weight ratio glycine to hydroxytyrosol is between 30:1 and 40:1, respectively, the weight ratio of L-taurine to hydroxytyrosol is between 20:1 and 50:1, respectively, the weight ratio of L-proline to hydroxytyrosol is between 1:1 and 10:1, respectively, the weight ratio of niacinamide to hydroxytyrosol is between 1:1 and 5:1, respectively, the weight ratio of pyridoxine to hydroxytyrosol is between 1:1 and 5:1, and the weight ratio of methylsulfonylmethane to hydroxytyrosol is between 10:1 and 30:1. In another example of this embodiment, the weight ratio N-acetylcysteine to hydroxytyrosol is between 20:1 and 25:1, respectively, the weight ratio glycine to hydroxytyrosol is between 30:1 and 40:1, respectively, the weight ratio of L-taurine to hydroxytyrosol is between 30:1 and 40:1, respectively, the weight ratio of L-proline to hydroxytyrosol is between 1:1 and 5:1, respectively, the weight ratio of niacinamide to hydroxytyrosol is between 1:1 and 2:1, respectively, the weight ratio of pyridoxine to hydroxytyrosol is between 1:1 and 2:1, and the weight ratio of methylsulfonylmethane to hydroxytyrosol is between 10:1 and 20:1.

Composition Formulations

Compositions containing LSF may be formulated in any conventional manner. Proper formulation is dependent upon the route of administration chosen. Suitable routes of administration include, but are not limited to, oral, parenteral (e.g., intravenous, intraarterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration.

Pharmaceutically acceptable carriers for use in the compositions of the present invention are well known to those of ordinary skill in the art and are selected based upon a number of factors: LSF concentration and intended bioavailability; the disease, disorder or condition being treated with the composition; the subject, his or her age, size and general condition; and the route of administration. Suitable carriers are readily determined by one of ordinary skill in the art (see, for example, J. G. Nairn, in: Remington's Pharmaceutical Science (A. Gennaro, ed.), Mack Publishing Co., Easton, Pa., (1985), pp. 1492-1517, the contents of which are incorporated herein by reference).

In general, nasal routes of administration are preferred. When administered nasally, these compositions are prepared according to techniques well known in the art of pharmaceutical formulation and may be prepared as solutions in saline, employing benzyl alcohol or other suitable preservatives, absorption promoters to enhance bioavailability, and/or other solubilizing or dispersing agents known in the art (see, for example, Ansel et al. (1999) Pharmaceutical Dosage Forms and Drug Delivery Systems (7th ed.).

The LSF containing compositions of the present invention may also be preferably formulated for parenteral administration, e.g., formulated for injection via intravenous, intraarterial, subcutaneous, rectal, subcutaneous, intramuscular, intraorbital, intracapsular, intraspinal, intraperitoneal, or intrasternal routes. The compositions of the invention for parenteral administration comprise an effective amount of LSF in a pharmaceutically acceptable carrier. Dosage forms suitable for parenteral administration include solutions, suspensions, dispersions, emulsions or any other dosage form which can be administered parenterally. Techniques and compositions for making parenteral dosage forms are known in the art.

Suitable carriers used in formulating liquid dosage forms for oral or parenteral administration include nonaqueous, pharmaceutically-acceptable polar solvents such as oils, alcohols, amides, esters, ethers, ketones, hydrocarbons and mixtures thereof, as well as water, saline solutions, dextrose solutions (e.g., DW5), electrolyte solutions, or any other aqueous, pharmaceutically acceptable liquid.

Suitable nonaqueous, pharmaceutically-acceptable polar solvents include, but are not limited to, alcohols (e.g., .alpha.-glycerol formal, .beta.-glycerol formal, 1,3-butyleneglycol, aliphatic or aromatic alcohols having 2-30 carbon atoms such as methanol, ethanol, propanol, isopropanol, butanol, t-butanol, hexanol, octanol, amylene hydrate, benzyl alcohol, glycerin (glycerol), glycol, hexylene glycol, tetrahydrofurfuryl alcohol, lauryl alcohol, cetyl alcohol, or stearyl alcohol, fatty acid esters of fatty alcohols such as polyalkylene glycols (e.g., polypropylene glycol, polyethylene glycol), sorbitan, sucrose and cholesterol); amides (e.g., dimethylacetamide (DMA), benzyl benzoate DMA, dimethylformamide, N-(.beta.-hydroxyethyl)-lactamide, N,N-dimethylacetamide amides, 2-pyrrolidinone, 1-methyl-2-pyrrolidinone, or polyvinylpyrrolidone); esters (e.g., 1-methyl-2-pyrrolidinone, 2-pyrrolidinone, acetate esters such as monoacetin, diacetin, and triacetin, aliphatic or aromatic esters such as ethyl caprylate or octanoate, alkyl oleate, benzyl benzoate, benzyl acetate, dimethylsulfoxide (DMSO), esters of glycerin such as mono, di, or tri-glyceryl citrates or tartrates, ethyl benzoate, ethyl acetate, ethyl carbonate, ethyl lactate, ethyl oleate, fatty acid esters of sorbitan, fatty acid derived PEG esters, glyceryl monostearate, glyceride esters such as mono, di, or tri-glycerides, fatty acid esters such as isopropyl myristate, fatty acid derived PEG esters such as PEG-hydroxyoleate and PEGhydroxystearate, N-methylpyrrolidinone, pluronic 60, polyoxyethylene sorbitol oleic polyesters such as poly(ethoxylated)30-60 sorbitol poly(oleate)2-4, poly(oxyethylene)15-20 monooleate, poly(oxyethylene)15-20 mono 12-hydroxystearate, and poly(oxyethylene)15-20 mono ricinoleate, polyoxyethylene sorbitan esters such as polyoxyethylene-sorbitan monooleate, polyoxyethylene-sorbitan monopalmitate, polyoxyethylene-sorbitan monolaurate, polyoxyethylene-sorbitan monostearate, and Polysorbate® 20, 40, 60 or 80 from ICI Americas, Wilmington, Del., polyvinylpyrrolidone, alkyleneoxy modified fatty acid esters such as polyoxyl 40 hydrogenated castor oil and polyoxyethylated castor oils (e.g., Cremophor® EL solution or Cremophor® RH 40 solution), saccharide fatty acid esters (i.e., the condensation product of a monosaccharide (e.g., pentoses such as ribose, ribulose, arabinose, xylose, lyxose and xylulose, hexoses such as glucose, fructose, galactose, mannose and sorbose, trioses, tetroses, heptoses, and octoses), disaccharide (e.g., sucrose, maltose, lactose and trehalose) or oligosaccharide or mixture thereof with a C4-C22 fatty acid(s)(e.g., saturated fatty acids such as caprylic acid, capric acid, lauric acid, myristic acid, palmitic acid and stearic acid, and unsaturated fatty acids such as palmitoleic acid, oleic acid, elaidic acid, erucic acid and linoleic acid)), or steroidal esters); alkyl, aryl, or cyclic ethers having 2-30 carbon atoms (e.g., diethyl ether, tetrahydrofuran, dimethyl isosorbide, diethylene glycol monoethyl ether); glycofurol (tetrahydrofurfuryl alcohol polyethylene glycol ether); ketones having 3-30 carbon atoms (e.g., acetone, methyl ethyl ketone, methyl isobutyl ketone); aliphatic, cycloaliphatic or aromatic hydrocarbons having 4-30 carbon atoms (e.g., benzene, cyclohexane, dichloromethane, dioxolanes, hexane, n-decane, n-dodecane, n-hexane, sulfolane, tetramethylenesulfon, tetramethylenesulfoxide, toluene, dimethylsulfoxide (DMSO), or tetramethylenesulfoxide); oils of mineral, vegetable, animal, essential or synthetic origin (e.g., mineral oils such as aliphatic or wax-based hydrocarbons, aromatic hydrocarbons, mixed aliphatic and aromatic based hydrocarbons, and refined paraffin oil, vegetable oils such as linseed, tung, safflower, soybean, castor, cottonseed, groundnut, rapeseed, coconut, palm, olive, corn, corn germ, sesame, persic and peanut oil and glycerides such as mono-, di- or triglycerides, animal oils such as fish, marine, sperm, cod-liver, haliver, squalene, squalane, and shark liver oil, oleic oils, and polyoxyethylated castor oil); alkyl or aryl halides having 1-30 carbon atoms and optionally more than one halogen substituent; methylene chloride; monoethanolamine; petroleum benzin; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (Solutol® HS-15, from BASF, Ludwigshafen, Germany); polyoxyethylene glycerol; sodium laurate; sodium oleate; or sorbitan monooleate.

A nasal preparation comprised of the composition described above can take a variety of forms for administration in nasal drops, nasal spray, gel, ointment, cream, powder or suspension, using a dispenser or other device as needed. A variety of dispensers and delivery vehicles are known in the art, including single-dose ampoules, atomizers, nebulizers, pumps, nasal pads, nasal sponges, nasal capsules, and the like.

More generally, the preparation can take a solid, semi-solid, or liquid form. In the case of a solid form, the components may be mixed together by blending, tumble mixing, freeze-drying, solvent evaporation, co-grinding, spray-drying, and other techniques known in the art. Such solid state preparations preferably provide a dry, powdery composition with particles in the range of between about 20 to about 500 microns, more preferably from 50 to 250 microns, for administration intranasally.

A semi-solid preparation suitable for intranasal administration can take the form of an aqueous or oil-based gel or ointment. For example, the components described above can be mixed with microspheres of starch, gelatin, collagen, dextran, polylactide, polyglycolide, or other similar materials that are capable of forming hydrophilic gels. The microspheres can be loaded with drug, and upon administration form a gel that adheres to the nasal mucosa.

In a preferred embodiment, the nasal preparation is in liquid form, which can include an aqueous solution, an aqueous suspension, an oil solution, an oil suspension, or an emulsion, depending on the physicochemical properties of the composition components. The liquid preparation is administered as a nasal spray or as nasal drops, using devices known in the art, including nebulizers capable of delivering selected volumes of formulations as liquid-droplet aerosols. For example, a commercially available spray pump with a delivery volume of 50 µL or 100 µL is available from, for example, Valois (Congers, N.Y.) with spray tips in adult size and pediatric size. In one embodiment, the LSF containing compositions are administered intranasally via an aerosol spray in a daily volume of between about 10 to 500 µL, more preferably between about 30 to about 200 µL.

The liquid preparation can be produced by known procedures. For example, an aqueous preparation for nasal administration can be produced by dissolving, suspending, or emulsifying the components in water, buffer, or other aqueous medium, or in a oleaginous base, such as a pharmaceutically-acceptable oil like olive oil, lanoline, silicone oil, glycerine fatty acids, and the like.

It will be appreciated that excipients necessary for formulation, stability, and/or bioavailability can be included in the preparation. Exemplary excipients include sugars (glucose, sorbitol, mannitol, sucrose), uptake enhancers (chitosan), thickening agents and stability enhancers (celluloses, polyvinyl pyrrolidone, starch, etc.), buffers, preservatives, and/or acids and bases to adjust the pH, and the like.

Methods

The LSF containing compositions and/or regimens of the present invention may be used in methods for the treatment of subjects having a variety of diseases. In some embodiments, the LSF containing compositions and/or regimens of the present invention may be used for the treatment of diseases or conditions associated with inflammation or oxidative stress. In some embodiments, the LSF containing compositions and/or regimens of the present invention may be used for the treatment or prevention of pulmonary edema, including exercise induced pulmonary hemorrhage (EIPH), or high-altitude pulmonary edema (HAPE).

In an embodiment, the treatment may be performed by administration of a spray or aerosol LSF containing compositions and/or regimens to the subject in need thereof. The treatment may be performed in conjunction with administration of other beneficial compositions, for example hydroxytyrosol-containing compositions according to U.S. Pat. No. 8,765,794, which is incorporated herein in its entirety. The treatment may be performed by administration of components in any order and in any combination. Further, the treatment may be performed by providing multiple administrations of the compositions. One skilled in the art will ascertain these variations in treatment regimens employing the LSF compositions and/or regimens disclosed herein.

As referred to in the methods of administering LSF compositions, such compositions include any LSF-based inhibitor of HDAC proteins. Suitable LSF-based inhibitor of HDAC proteins include, for example, LSF, a LSF derived compound, a LSF substituted compound, a LSF metabolite (originating from a prodrug), and combinations of the same. A LSF composition may further include a chemotherapeutic agent, carrier, diluent and/or other pharmaceutically acceptable delivery agents or the like.

The methods of the invention may be further applicable to other conditions that are associated with inflammation or oxidative stress, such as for example, ankylosing spondylitis, multiple sclerosis, Crohn's disease, psoriasis, psoriatic arthritis, rheumatoid arthritis, and scleroderma.

The combination of LSF and optionally one or more of hydroxytyrosol, oleuropein, N-acetylcysteine, L-proline, glycine, and taurine according to methods of the invention results in at least additive effects, preferably synergistic effects. The combinational therapy according to the invention results in a greater reduction of symptoms, including for example greater reduction of fluid in the lungs, greater reduction of hypoxia, and greater reduction of inflammation and/or inflammatory mediators, and/or other indicators of improved treatment for a regimen disclosed herein, in comparison to any compound alone.

Inhibition and Inactivation of Histone Deacetylases

The activity of HDACs is regulated on multiple levels including protein-protein interactions, post-translational modification by phosphorylation, acetylation, sumoylation and proteolysis, subcellular localization, and a variety of metabolic cofactors, including for example zinc. Without being bound to any particular theory, compositions and methods of the present invention may inhibit HDACs, by interfering with or blocking interactions with substrates or other proteins. In one aspect, LSF may occupy, mask, or otherwise block access to the catalytic site of the HDAC.

In one aspect, the LSF containing compositions specifically inhibit Class I HDACs, and more particularly specifically inhibit HDAC8. Thus, LSF containing compositions of the present invention may be used for particular HDAC inhibition.

LSF Interaction with Histone Deacetylase Enzymes (HDACs)

Without being limited to a particular theory, it is believed that LSF interacts directly with HDACs, including specific interaction with HDAC8, in a manner that inhibits the deacetylase activity of the enzyme. In the alternative, LSF may block peptide ligand binding or alter the conformation of the ligand binding site of HDACs, including HDAC8, or interacting with key amino acid residues that affect substrate binding by HDACs, including HDAC8. The invention therefore embodies any derivative of LSF or glucosinolates, or structural mimics or homologues thereof, that exhibits binding and/or inhibition characteristics similar to LSF.

Figure 2:
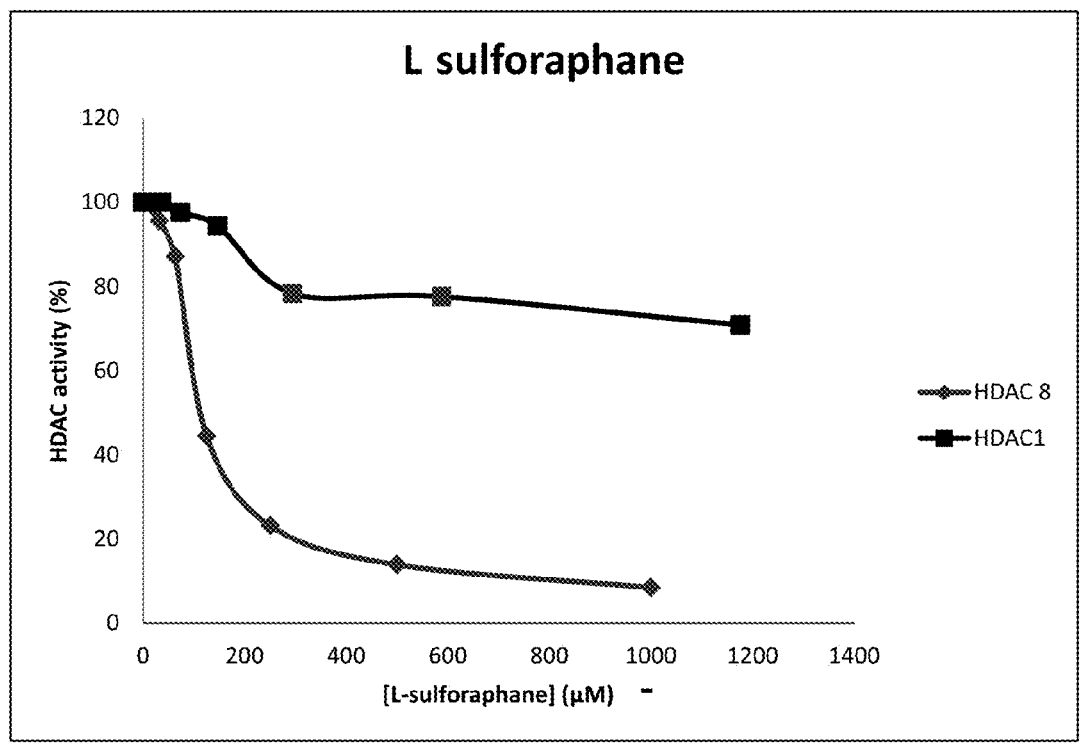
FIG. 2 shows inhibition of HDACs 1 and 8 by L-sulforaphane.
Figure 3A:
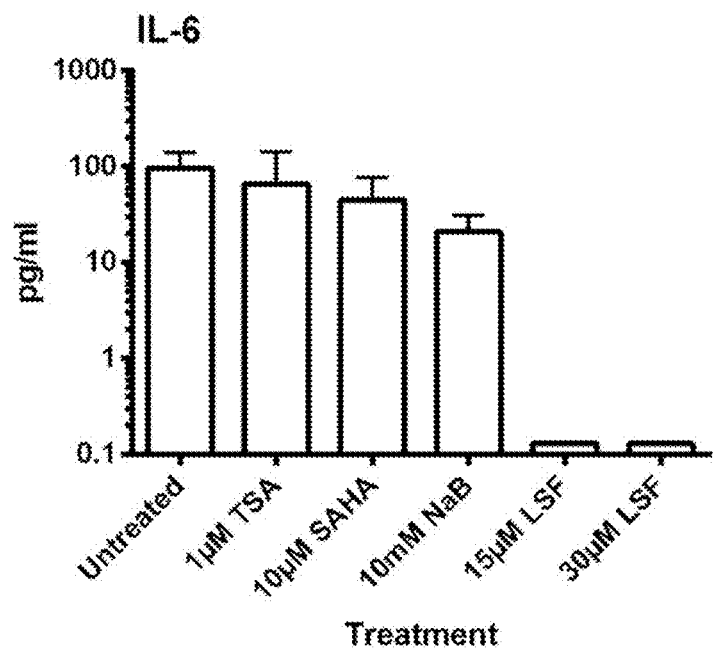
FIG. 3 (A-F) shows the effect of L-sulforaphane on cytokine and chemokine secretion from peripheral blood mononuclear cells (PBMC). PBMC were stimulated in vitro with 1 µM Trichostatin A (TSA), 10 µM suberoyanilide hydroxamic acid (SAHA), 10 mM sodium butyrate (NaB), 15 μM LSF, 30 μM LSF or PBS (unstimulated), and production of (A) IL-6, (B) IL-1β, (C) IL-8, (D) IP-10 (E) MIP-1β, and (F) TNF-α were measured FIG. 4 (A-F) shows histological and immunofluorescence analyses of the effect of L-sulforaphane on ovalbumin-induced allergic airways disease. (A-C) show H&E stained lung/bronchial tissue sections from mice treated with (A) saline (control), (B) vehicle control and (C) 5 mg/kg L-sulforaphane following challenge by Ovalbumin nebulisation. (D-F) shows immunofluorescence microscopy images of lung/bronchial tissue sections from mice treated with (D) saline (control), (E) vehicle control and (F) 5 mg/kg L-sulforaphane following challenge by Ovalbumin nebulization.
Figure 3B:
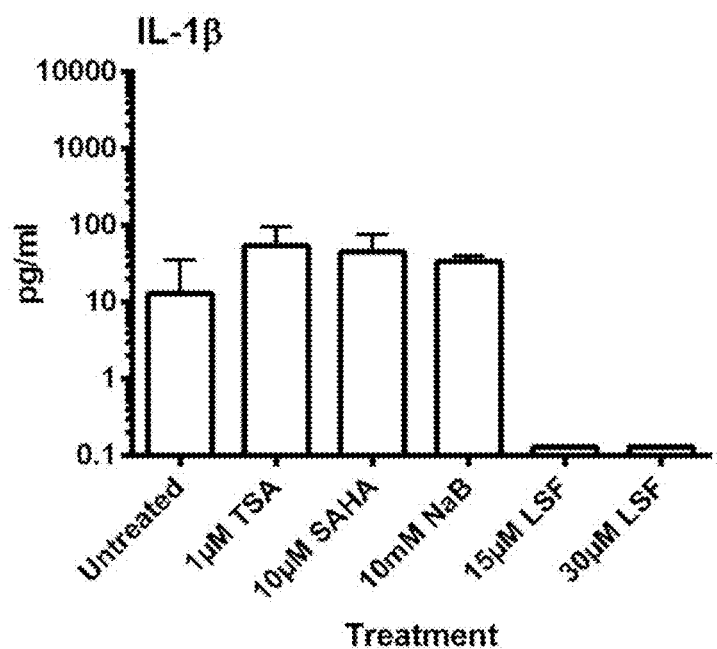
Figure 3C:
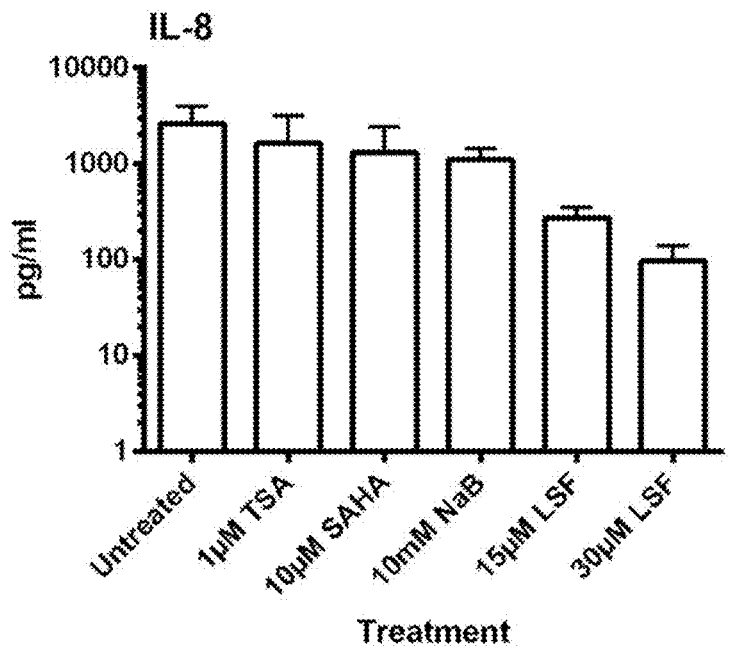
Figure 3D:
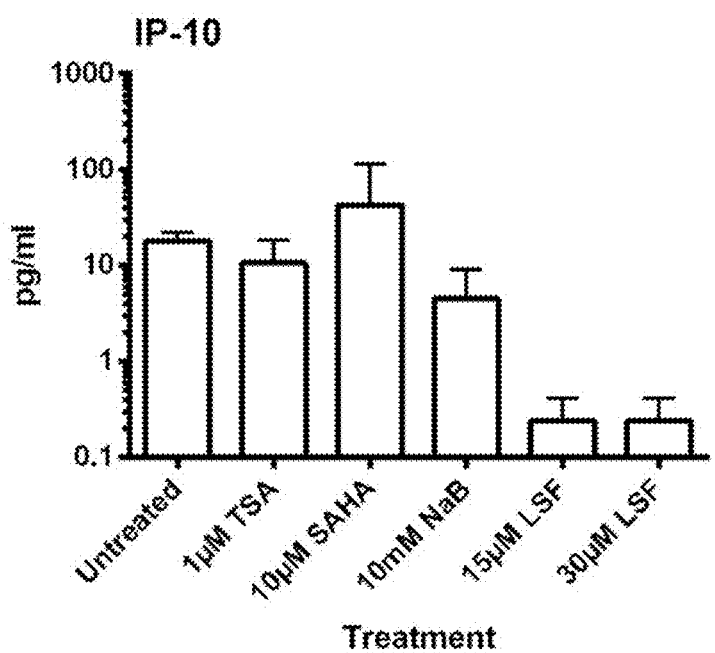
Figure 3E:
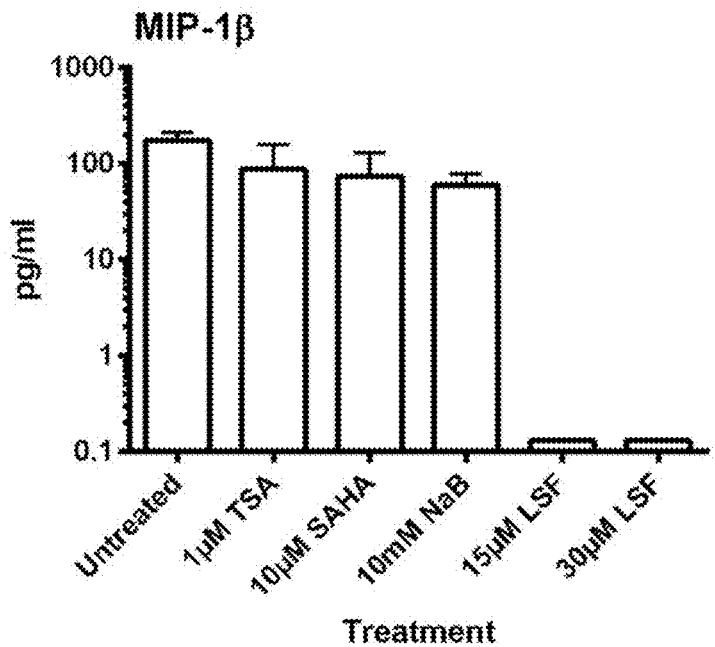
Figure 3F:
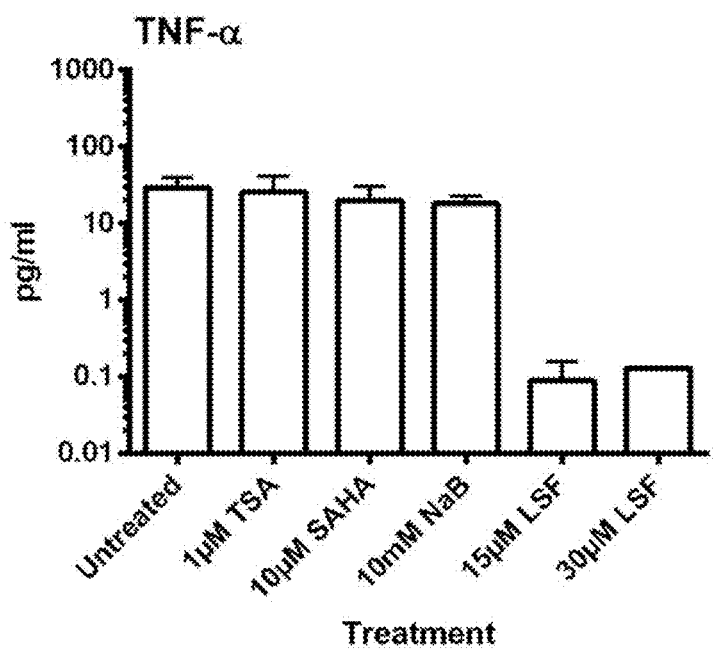

As demonstrated by this invention, LSF inhibits the enzymatic activity of HDAC8 (FIG. 2). Unlike other inhibitors of HDAC8, LSF is a naturally occurring compound, lacking the substantial toxic side effects of other inhibitors. According to the invention, HDACs, including HDAC8, is inhibited by exposure to compositions comprising LSF, derivatives of LSF, or structural mimics or homologues thereof. This inhibition of HDACs prevents inflammatory responses, including the production of inflammatory mediators. In addition, LSF is known to have potent antioxidant effects by activation of the Nrf2-ARE detoxification pathway. Although not bound by this exemplary embodiment, LSF can be provided in order to inhibit enzymatic activity, prevent association with co-factors or partner proteins, or otherwise inhibit HDACs, or to reduce oxidative stress in target cells or tissues, thereby treating or preventing conditions associated with inflammation or oxidative stress.

It is understood that prevention or treatment of conditions associated with inflammation, including pulmonary edema and EIPH, by LSF, or derivatives/equivalents of LSF, can be by one or more of these mechanisms.

Methods of Treating Diseases or Conditions Involving Inflammation and/or Oxidative Stress LSF reduces the production of inflammatory mediators, including cytokines and chemokines. Methods according to the present invention may include administration of LSF containing compositions to a subject in need thereof in order to block or reduce an inflammatory response either systemically or at a specific location (i.e. in the airways and lungs).

In a more particular aspect, the methods of the present invention may involve modulation of genes involved in type I (alpha/beta) and type II (gamma) interferon (IFN) signaling. Such modulation may be increasing or decreasing the expression of one or more of the genes. Other methods of the present invention may involve modulation (i.e. increasing or decreasing expression) of one or more genes due to upregulation of general transcription factors (POL2, TAF1) and/or downregulation of STAT1, STAT2 and RAD21 targets.

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

L-Sulforaphane Inhibits Specific Metal-Dependent Histone Deacetylase Enzymes

Summary

L-sulforaphane exhibits specific affinity for binding particular histone deacetylase enzymes (HDACs), and specific inhibition of HDAC8.

Methods

The binding of L-sulforaphane to the 11 metal dependent histone deacetylase enzymes was performed using the epigenetic assay services. Experiments were performed in comparison to the prototypical histone deacetylase inhibitor, Trichostatin A.

Results and Discussion:

The binding constant and hillslope for LSF in comparison to Trichostatin A is shown in Table 1. The findings indicate specific binding of LSF to HDACs 3, 6, 7 and 8 which is more subtle than Trichostatin A. The binding of LSF to HDAC8 is most pronounced and indicated in FIG. 1.

TABLE 1

Binding constants for LSF to metal-dependent histone deacetylases.

| HDAC | | LSF | Trichostatin A |
|---|---|---|---|
| HDAC-1 | HILLSLOPE | | −0.79 |
| | IC50 (M) | | 3.41E−09 |
| HDAC-2 | HILLSLOPE | | −0.93 |
| | IC50 (M) | | 1.38E−08 |
| HDAC-3 | HILLSLOPE | −0.20 | −0.49 |
| | IC50 (M) | 0.02053 | 1.16E−08 |
| HDAC-4 | HILLSLOPE | | −0.24 |
| | IC50 (M) | | 1.24E−07 |
| HDAC-5 | HILLSLOPE | | −0.77 |
| | IC50 (M) | | 7.61E−09 |
| HDAC-6 | HILLSLOPE | −0.88 | −1.16 |
| | IC50 (M) | 1.02E−03 | 1.39E−09 |
| HDAC-7 | HILLSLOPE | −0.41 | −0.49 |
| | IC50 (M) | 5.81E−03 | 4.17E−08 |
| HDAC-8 | HILLSLOPE | −0.88 | −0.64 |
| | IC50 (M) | 8.27E−05 | 2.10E−07 |
| HDAC-9 | HILLSLOPE | | −0.45 |
| | IC50 (M) | | 2.49E−08 |
| HDAC-10 | HILLSLOPE | | −0.84 |
| | IC50 (M) | | 1.27E−08 |
| HDAC-11 | HILLSLOPE | | −0.59 |
| | IC50 (M) | | 1.05E−08 |

The inhibition of HDAC1 and HDAC8 enzymatic activity by L-sulforaphane were examined using the HDAC1 and HDAC8 inhibitor Screening Assay Kits from Cayman Chemical, respectively, using the manufacturer's instructions. The results of these assays shown in FIG. 2, highlight the specificity of L-sulforaphane for HDAC8 compared to HDAC1.

Example 2

Anti-Inflammatory and Antioxidant Effects of L-Sulforaphane

Summary

L-sulforaphane reduces cytokine and chemokine release from peripheral blood mononuclear cells.

Methods

Cryopreserved peripheral blood mononuclear cells (PBMC) from healthy adult donors were rapidly thawed in a 37° C. water-bath until approximately 50% thawed and slowly re-suspended in 10 mL of RPMI-1640 medium supplemented with 20 mmol/L HEPES (pH 7.4), 10% (v/v) fetal bovine serum, 2 mmol/L L-glutamine, and 20 µg/mL gentamicin (GIBCO-Invitrogen, USA). The PBMC suspension was centrifuged for 5 minutes at 700 g, after which the supernatant was discarded and cells were re-suspended in fresh RPMI-1640.

The levels of TNF-α, IL-1β, IL-6, IL-8, MIP-1β and IP-10 in supernatants from PBMC samples stimulated in vitro with 1 µM Trichostatin A (TSA), 10 µM suberoyanilide hydroxamic acid (SAHA), 10 mM sodium butyrate (NaB), 15 µM LSF, 30 µM LSF or PBS (unstimulated) were measured using the MAP Human cytokine/chemokine kit (Millipore, USA) as per manufacturer's instructions. The 96-well filter plate was pre-wet by adding 200 µL/well of assay buffer and incubated on a shaker for 10 mins at RT. Assay buffer was removed by vacuum and 25 µL of the standard and quality control reagents were added in duplicate with a six-point standard curve prepared using the human cytokine/chemokine standard reagent using 1:5 serial dilutions in the range 10,000 pg/mL-3.2 pg/mL and PBS (−) alone as the background. Undiluted supernatants were added in duplicate (25 µL/well) followed by 25 µL/well of the pre-mixed cytokine/chemokine beads to all wells and the plate incubated overnight on a plate shaker at 4° C. The following day, standards, controls and sample volumes were removed by vacuum filtration and washed two times with 200 µL/well wash buffer and 25 µL/well biotinylated detection antibodies added to all wells and incubated on a plate shaker for 1 hr at RT. The reaction was developed by adding 25 µL/well of streptavidin-phycoerythrin to all wells and incubated for a further 30 min at RT on a plate shaker. The plate was then washed twice with assay buffer and a final volume of 150 µL of sheath fluid added to all wells and beads re-suspended. The plate was read using a Luminex 100™ IS instrument and software package (Luminex Corporation, Texas, USA) and the mean fluorescent intensity data analyzed using a weighted 5-parameter logistic method to yield cytokine/chemokine concentrations (pg/mL) in the supernatants.

Results

The results shown in FIG. 3 indicate that treatment with L-sulforaphane produces a reduction in the chemokines and cytokines examined, with more pronounced effects than the classical histone deacetylase inhibitors, Trichostatin A (TSA), suberoyl anilide hydroxamic acid (SAHA), and sodium butyrate (NaB).

Example 3

L-Sulforaphane Prevents Allergic Airways Disease and Naphthalene-Induced Airway Epithelial Damage Summary Administration of LSF prevented the damage and detrimental effects in mouse models of allergic airway reactions and chemical-induced airway epithelial damage.

Methods

An established model of ovalbumin (OVA)-induced AAD was used as previously described (Temelkovski et al., 1998). This model includes many of the pathological features of human asthma including increased allergic responses indicated by increased immunoglobulin E against OVA (OVA-specific IgE), epithelial remodeling, goblet cell metaplasia, subepithelial collagen deposition (fibrosis) and airway hyperresponsiveness. Briefly, 6-8 week old mice (Balb/c) were sensitized with 10 mg of grade V OVA (Sigma Chemical, St Louis, Mo., USA) and 1 mg of aluminum potassium sulfate adjuvant (alum) in 500 µl saline intraperitoneally on day 0 and 14 and then challenged with nebulized 2.5% (w/v) OVA in saline three days per week for six weeks to establish AAD. Ovalbumin-exposed mice were treated with 5 mg/kg L-sulforaphane (OVA-LSF, n=5) or vehicle control (OVA-VEH, n=15) intraperitoneally following each OVA nebulization (3 days per week for 6 weeks). A third group of mice, sensitized with saline/alum on days 0 and 14 and nebulized with saline 3 days per week for 6 weeks (n=15), served as additional controls. All experimental procedures were approved by the Institutional Animal Ethics Committee and followed the Australian Guidelines for the Care and Use of Laboratory Animals for Scientific Purposes.

Morphometric analysis was performed on H&E stained lung tissue sections. Images of lung tissue sections were captured using a Digital camera (Q Imaging, Burnaby, British Columbia, Canada). A minimum of five bronchi measuring 150-350 µm luminal diameter were analyzed per mouse using Image Pro-Discovery software (Media Cybernetics, Silver Spring, Md.), which was calibrated with a reference micrometer slide. The thickness of the bronchial epithelial layer was measured by tracing around the basement membrane and the luminal surface of epithelial cells using a digitizer (Aiptek, Irvine, Calif.) and calculating the mean distance between the lines by Image Pro-Discovery software (Media Cybernetics).

For immunofluorescence, tissue sections were blocked for 1 hour using Superblock (Thermo Scientific) at room temperature followed by a 5 minute wash using 0.5% Tween 20, 0.1% Triton X-100 in phosphate buffered saline (PBS-TT). Tissues were exposed to primary monoclonal antibodies anti-Annexin V (rabbit; Epitomics) and anti-histone deacetylase 8 (mouse, Sigma), diluted in 1% BSA (1:500). Primary antibodies were incubated in a dark humidified chamber overnight. Following three 10 minute washes in PBS-TT, tissues were incubated with secondary antibodies, goat anti-mouse Alexa 488 (Molecular Probes) and goat anti-rabbit 546 (Molecular Probes) diluted in 1% BSA (1:500) in a dark humidified chamber for one hour on a rotating platform. Following three 10 minute washes in PBS-TT, tissues were mounted using Prolong Gold Antifade with DAPI (Invitrogen Molecular Probes). Slides were incubated overnight at 4° C. before imaging. Images were acquired using an Olympus BX61 fluorescence microscope automated with FVII Camera.

For studies using naphthalene-induced airway epithelial damage by L-sulforaphane, female wild type (C57B6J) mice between the ages of six to eight weeks were injected with naphthalene (200 mg/kg) intraperitoneally (ip) or with corn oil (vehicle control, volumes were normalized for body weight). Mice were monitored for up to 72 hours (the point by which re-epithelialization has occurred) and mice were culled at 24 and 72 hours for analysis. The treatment groups received an ip injection of 5 mg/kg L-sulforaphane (LSF) or 1 mg/kg dexamethasone (DEX). Histological analysis was performed on hematoxylin and eosin or Mason's trichrome stained lung sections.

Results

Figure 5A:
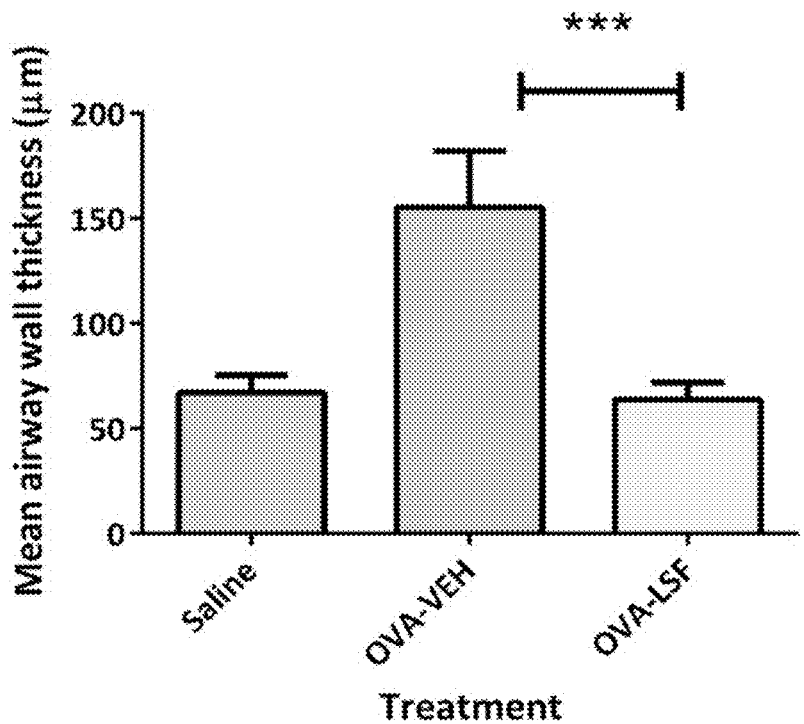
FIG. 5 (A-B) shows effects of L-sulforaphane on (A) mean airway wall thickness and (B) epithelium thickness in a mouse model of allergic airways disease.
Figure 5B:
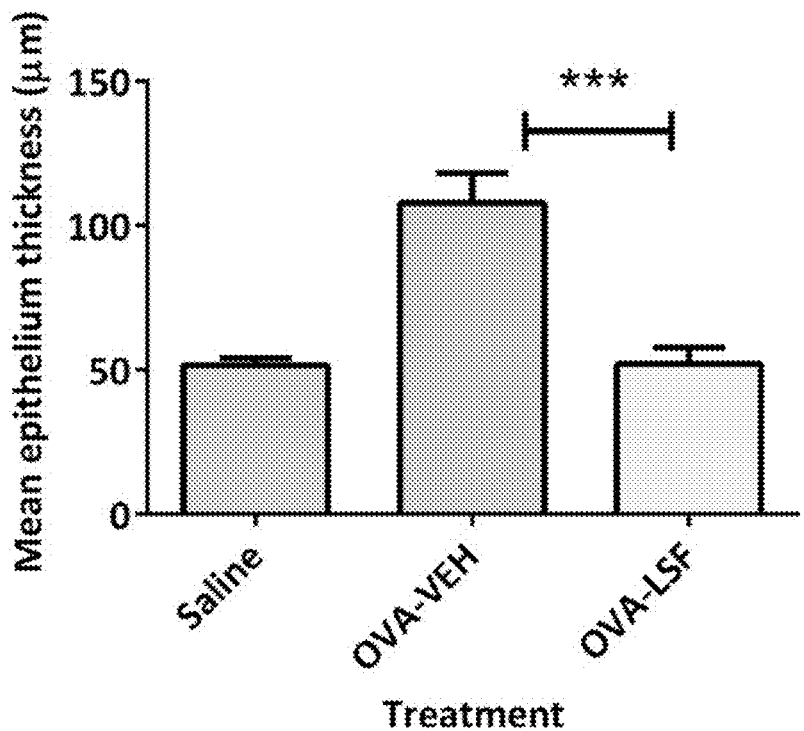

Histological examination indicates that L-sulforaphane has beneficial effects compared to ovalbumin-sensitized mice with reductions in goblet cell hyperplasia, inflammation and airway wall thickness being observed (FIG. 4A-C). Mean airway wall thickness and epithelial thickness were quantitated by morphometric analysis (FIG. 5). Strong staining of Annexin V was found largely in bronchial epithelium and peribronchial inflammatory cells in mice treated with OVA-VEH. Weak Annexin V staining was present in mice treated with OVA-LSF indicating a reduction in apoptosis. In contrast, Annexin V staining was not observed in the epithelium in saline control mice (FIG. 4D-F).

Figure 6A:
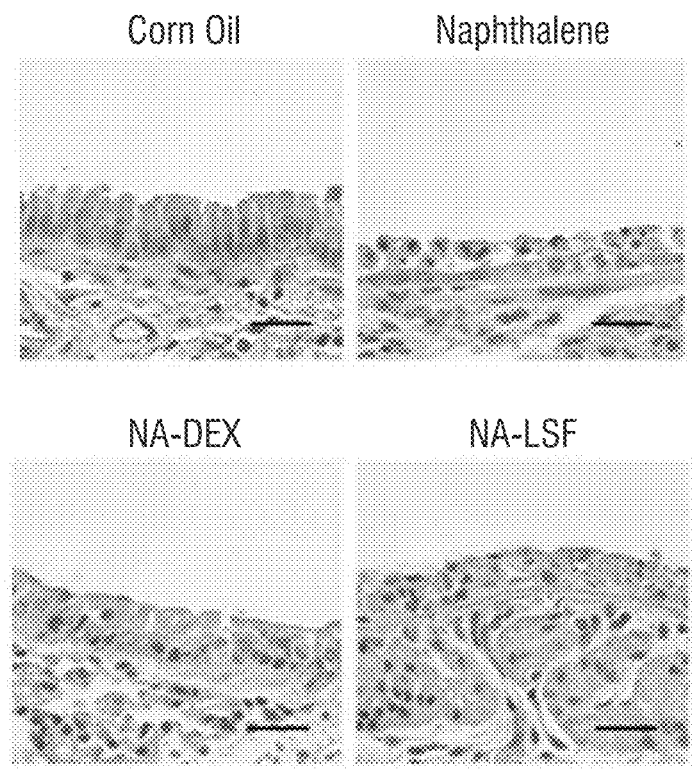
FIG. 6 (A-B) shows L-sulforaphane (LSF) reduction of naphthalene-induced epithelial denudation at 24 hours post-naphthalene injection with analogous efficacy to dexamethasone. (A) Representative hematoxylin and eosin stained lung sections. (B) Quantitation of histological examination of stained lung sections. Corn Oil: CO; Naphthalene: NA; dexamethasone: DEX; L-sulforaphane: LSF.
Figure 6B:
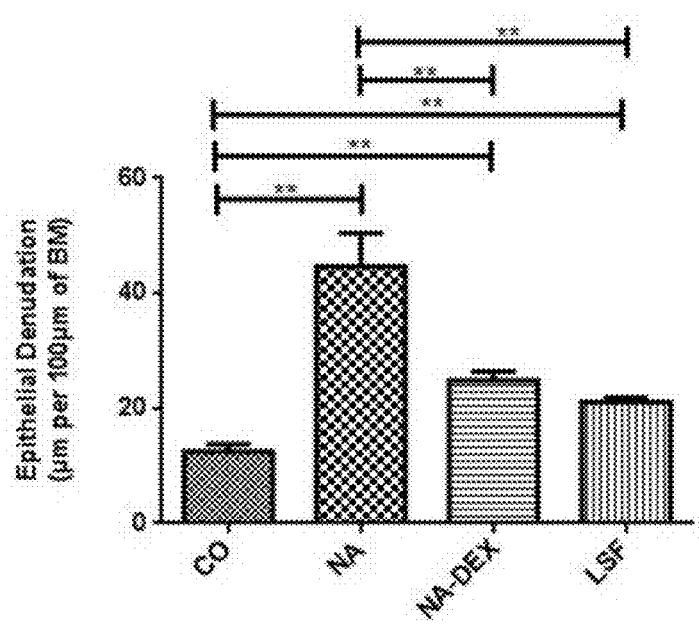
Figure 7A:
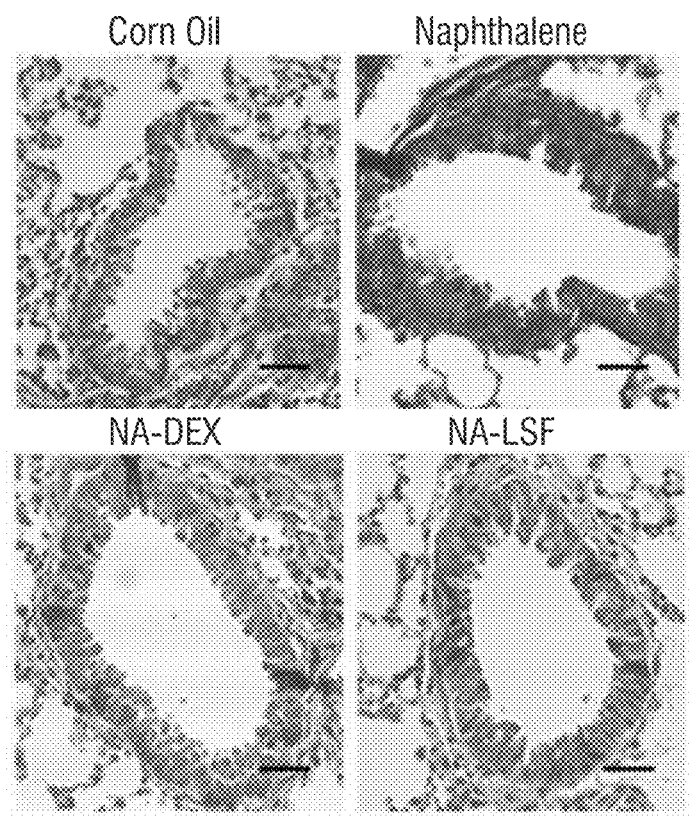
FIG. 7 (A-B) L-sulforaphane (LSF) reduces naphthalene-induced thickening of the lamina reticularis at 72 hours post-naphthalene injection with analogous efficacy to dexamethasone. (A) Representative Mason's trichrome stained lung sections. (B) Quantitation of histological examination of stained lung sections. Corn Oil: CO; Naphthalene: NA; dexamethasone: DEX; L-sulforaphane: LSF.
Figure 7B:
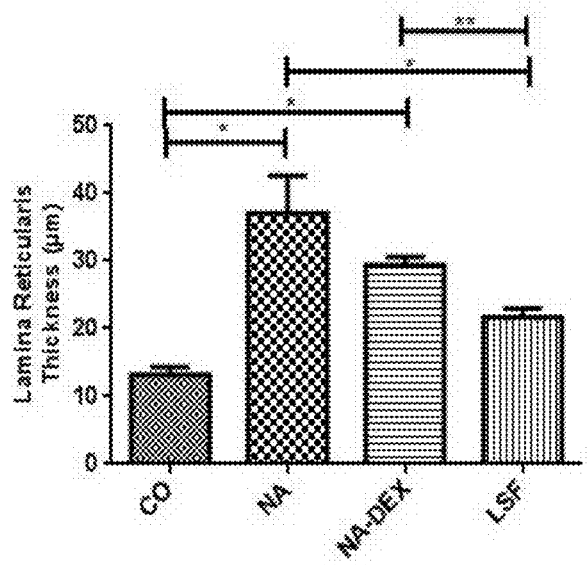

Histological examination indicates that L-sulforaphane reduces epithelial denudation at 24 hours to a level which analogous to that observed with the glucocorticoid dexamethasone (FIG. 6). Mason's trichrome staining indicates that L-sulforaphane reduces lamina reticularis thickness at 72 hours with efficacy similar to that of dexamethasone (FIG. 7).

Example 4

Protection of Cardiac Myocytes by Doxorubicin-Induced DNA Damage by L-Sulforaphane Using DNA Double-Strand Breaks as a Model (γH2AX Foci)

Methods

Rat embryonic ventricular myocardial H9c2 cells were obtained from the American Type Culture Collection and were grown as monolayers in Dulbecco's modified Eagle's medium (DMEM), containing 10% fetal bovine serum (FBS, In Vitro Technologies, Victoria, Australia), 100 U//ml penicillin and 100 µg/ml streptomycin (Invitrogen, Carlsbad, Calif., US), at 37° C. in a humidified atmosphere with 5% $CO_2$. Prior to confluence (typically 60-70%), cells were passaged using 0.5% trypsin-EDTA (Invitrogen) and centrifugation (250×g for 5 minutes) and seeded at ratios of 1:2 or 1:3 in DMEM containing 10% FBS for 24 or 48 hours. Cells were then cultured in DMEM containing 10 nM all-trans-retinoic acid (Sigma-Aldrich, St. Luis, Mo., US) for 7 days and the culture media was changed daily to obtain cardiac myocytes. Cells were incubated with 1 µM doxorubicin for 1 hour, washed twice with phosphate buffered saline without calcium and magnesium and were incubated for a further 24 hours in fresh media. To examine the effects of L-sulforaphane, H9c2 cells were pre-treated with 0, 10, 15 and 30 µM for 24 hours prior to treatment with doxorubicin. The number of γH2AX foci in H9c2 cell nuclei were quantitated as described previously (Mah et al., 2010).

Results

Figure 8:
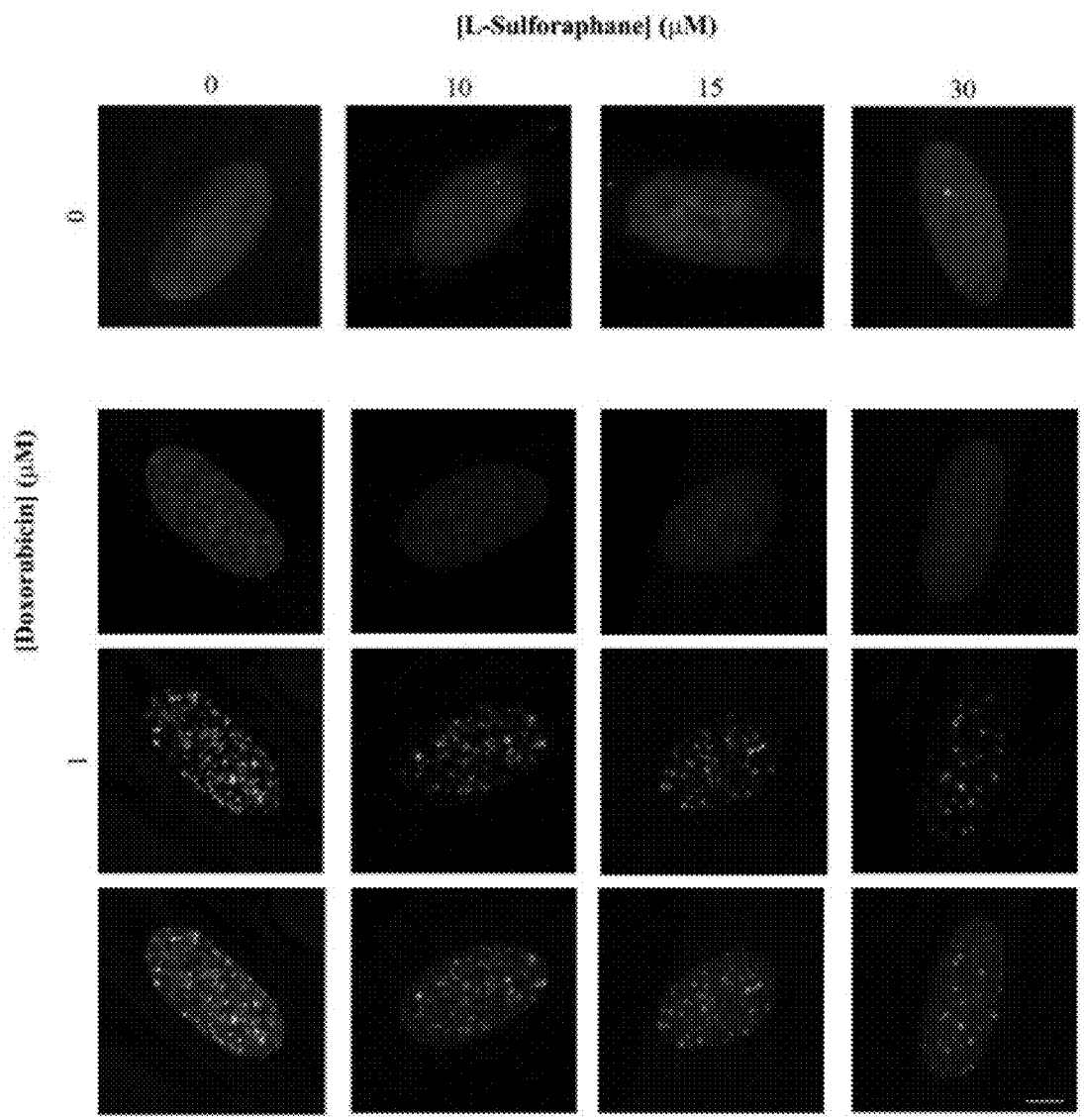
FIG. 8 shows L-Sulforaphane (LSF) attenuates doxorubicin-induced accumulation of γH2AX foci in H9c2 cells Immunofluorescence visualization of γH2AX foci (discrete foci in DAPI stained nuclei) in H9c2 cells pre-treated with 0, 10, 15 and 30 μM for 24 hours prior to treatment with doxorubicin.
Figure 9:
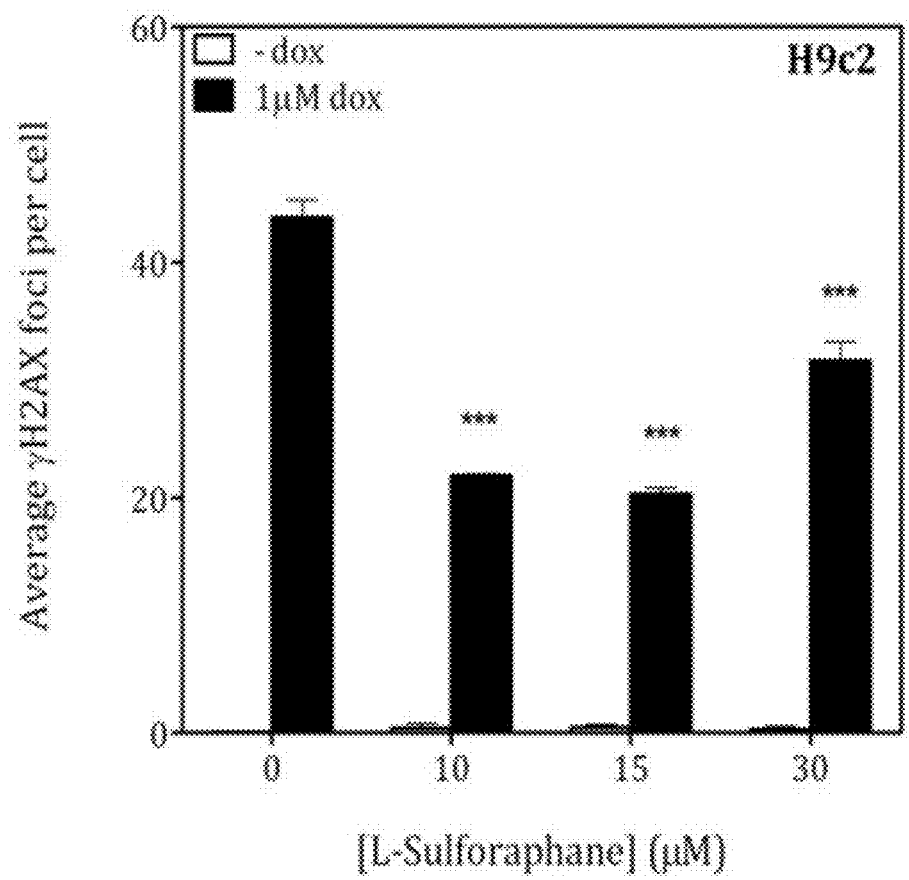
FIG. 9 shows L-Sulforaphane (LSF) attenuates doxorubicin-induced accumulation of γH2AX foci in H9c2 cells. Quantification of γH2AX foci (discrete foci in DAPI stained nuclei) in H9c2 cells pre-treated with 0, 10, 15 and 30 μM for 24 hours prior to treatment with doxorubicin.

Representative immunofluorescence microscopy images of H9c2 cells were pre-treated with 0, 10, 15 and 30 µM for 24 hours prior to treatment with doxorubicin are shown in FIG. 8. The results were quantified, and are presented in FIG. 9. The findings indicate that L-sulforaphane (LSF) attenuates doxorubicin-induced accumulation of γH2AX foci in H9c2 cells indicating potent antioxidant effects.

Example 5

Downregulation of Innate Immune and Inflammatory Pathways in PBMC by L-Sulforaphane Summary Horse PBMC were treated LSF or control in triplicate were analysed with mRNAseq. The sequencing run generated 161 million sequence tags that were used to measure the abundance of transcripts. Over 5,000 differentially regulated genes were identified. Pathways related to interferon signalling, STAT1/2 targets and autoimmune/auto-inflammatory diseases were strongly downregulated, suggesting that LSF has a potential to be a potent anti-inflammatory therapeutic. The expression of CD markers, immunoglobulin containing genes and interleukins are also strongly down-regulated.

Methods

RNA Isolation

RNA was isolated from trizol homogenates using the recommended organic phase separation technique followed by precipitation with isopropanol and resuspension in RNase free water. RNA was analysed on the MultiNA bioanalyzer (Shimadzu).

mRNA Sequencing

NEBNext® Poly(A) mRNA Magnetic Isolation Module was used to enrich mRNA from 1 µg of total RNA. We used the NEBNext® Ultra™ Directional RNA Library Prep Kit for Illumina® to generate barcoded libraries. Libraries were validated on the MultiNA bioanalyzer (Shimadzu) and pooled to equimolar ratios for sequencing. The pooled library was sequenced at the Australian Genome Research Facility (Melbourne) on Illumina HiSeq2500 instrument with version 4 single end flow cell for 60 cycles.

Bioinformatics Analysis

Data Processing and Technical Quality Control

Sequence data underwent quality trimming to remove low quality bases from the 3' end of reads using FASTXToolkit (version 0.0.14) using a Phred quality threshold of 20 and minimum 20 nt read length. STAR version 3.2.0.1 [PMID: 23104886] was used to align reads to the Horse genome (Equus_caballus.EquCab2.dna.toplevel.fa) downloaded from Ensembl. We used Ensembl version 77 gene annotations (Equus_caballus.EquCab2.77.gtf). Exonmapped reads were counted using featureCounts version 1.4.2 [PMID: 24227677]. Genes with fewer than 10 reads per sample on average were excluded from downstream analysis. Statistical analysis of differential gene expression was conducted using edgeR software version 0.20 with the default settings [PMID: 19910308]. To facilitate pathway analysis, horse gene identifiers were mapped to human gene names using horse-human homolog relationship table downloaded from Ensembl BioMart. Pathway analysis was performed using GSEAP software version gsea22.1.0 using the unweighted "classic" scoring scheme. Gene sets for pathway analysis were downloaded from MSigDB. ENCODE and Mouse ENCODE transcription factor binding site (TFBS) data were mined to generate gene sets of transcription factor targets that were also queried using GSEAP as described in the supplementary material. False discovery rate (FDR) adjusted p-values ≤0.05 were considered significant.

Results

Nearly all reads (99.93%) passed QC filtering and 83.5% of reads could be uniquely aligned. Alignment statistics are shown in Table 2.

TABLE 3

Top differnetially regulated genes.

| Ensembl Accession | GeneName | Log2 Fold Change | Log2 CPM | Adj P-value |
|---|---|---|---|---|
| ENSECAG00000022834 | WDR59 | 2.19 | 7.47 | 2.50E−187 |
| ENSECAG00000020307 | DENND2A | 3.67 | 5.67 | 2.30E−186 |
| ENSECAG00000021598 | ZFAND2A | 2.22 | 6.93 | 1.30E−182 |
| ENSECAG00000015982 | TXNRD1 | 2.13 | 9.70 | 3.80E−159 |
| ENSECAG00000014974 | GSAP | 2.00 | 7.78 | 2.80E−149 |
| ENSECAG00000022696 | SLC7A11 | 2.34 | 9.33 | 3.60E−137 |
| ENSECAG00000021447 | ASPH | 1.93 | 7.46 | 1.60E−132 |
| ENSECAG00000015342 | IL8 | 3.54 | 9.79 | 4.70E−111 |
| ENSECAG00000024408 | STAC2 | 3.38 | 4.53 | 5.90E−102 |
| ENSECAG00000000362 | STXBP5 | 1.57 | 8.42 | 3.30E−101 |
| ENSECAG00000023011 | RIPK2 | 2.01 | 6.96 | 2.50E−097 |
| ENSECAG00000014513 | TNFSF15 | 2.40 | 4.87 | 3.00E−094 |
| ENSECAG00000011797 | MN-SOD | 1.93 | 9.62 | 6.20E−093 |
| ENSECAG00000003192 | FTL | 1.51 | 9.74 | 1.10E−092 |
| ENSECAG00000024482 | ME1 | 1.47 | 7.54 | 2.10E−092 |
| ENSECAG00000013324 | TXN | 1.87 | 11.06 | 2.50E−091 |
| ENSECAG00000014514 | TUBA4A | 1.30 | 8.38 | 5.80E−088 |
| ENSECAG00000013560 | OSGIN2 | 1.88 | 6.08 | 1.70E−086 |
| ENSECAG00000007922 | KCNJ2 | 2.06 | 6.82 | 3.70E−086 |
| ENSECAG00000008693 | PTPN12 | 1.43 | 8.67 | 7.40E−081 |

TABLE 2

Alignment set statistics.

| Sample | Ctrl1 | Ctrl2 | Ctrl3 | LSF1 | LSF2 | LSF3 |
|---|---|---|---|---|---|---|
| Total reads | 23184730 | 24378587 | 31178787 | 24141494 | 29984514 | 28352005 |
| QC passed reads | 23170012 | 24362373 | 31156618 | 24125584 | 29962232 | 28332079 |
| Average input read length | 59 | 59 | 59 | 59 | 59 | 59 |
| Uniquely mapped reads number | 19186428 | 19603100 | 25257061 | 20424251 | 25531078 | 24544230 |
| Uniquely mapped reads % | 82.82% | 80.45% | 81.07% | 84.64% | 85.22% | 86.63% |
| Average mapped length | 59.3 | 59.3 | 59.3 | 59.3 | 59.3 | 59.3 |
| Number of splices: Total | 1532824 | 1495490 | 1878671 | 1472027 | 1669309 | 1947980 |
| Number of splices: GT/AG | 1516298 | 1479500 | 1858339 | 1455716 | 1650330 | 1926500 |
| Number of splices: GC/AG | 10147 | 9863 | 12591 | 10076 | 11347 | 13298 |
| Number of splices: AT/AC | 867 | 788 | 994 | 775 | 917 | 1097 |
| Number of splices: Non-canonical | 5512 | 5339 | 6747 | 5460 | 6715 | 7085 |
| Mismatch rate per base, % | 0.31% | 0.38% | 0.32% | 0.36% | 0.29% | 0.35% |
| Deletion rate per base | 0.01% | 0.01% | 0.01% | 0.01% | 0.01% | 0.01% |
| Deletion average length | 2.5 | 2.48 | 2.48 | 2.54 | 2.56 | 2.56 |
| Insertion rate per base | 0.01% | 0.01% | 0.01% | 0.01% | 0.01% | 0.01% |
| Insertion average length | 2.5 | 2.53 | 2.51 | 2.52 | 2.54 | 2.51 |
| Number of reads mapped to multiple loci | 2990229 | 3670724 | 4401558 | 2718150 | 3141640 | 2673452 |
| % of reads mapped to multiple loci | 12.91% | 15.06% | 14.13% | 11.27% | 10.50% | 9.43% |
| Number of reads mapped to too many loci | 25775 | 26430 | 34890 | 30008 | 39826 | 32422 |
| % of reads mapped to too many loci | 0.11% | 0.11% | 0.11% | 0.12% | 0.13% | 0.11% |
| Assigned | 8073651 | 8046910 | 10159013 | 7874621 | 9115250 | 10248009 |
| Unassigned_Ambiguity | 10280 | 10496 | 13343 | 9156 | 10743 | 12572 |
| Unassigned_MultiMapping | 0 | 0 | 0 | 0 | 0 | 0 |
| Unassigned_NoFeatures | 11102497 | 11545694 | 15084705 | 12540474 | 16405085 | 14283649 |
| Unassigned_Unmapped | 0 | 0 | 0 | 0 | 0 | 0 |
| Unassigned_MappingQuality | 11342903 | 14213425 | 16314170 | 9907186 | 11215053 | 9364434 |
| Unassigned_FragmentLength | 0 | 0 | 0 | 0 | 0 | 0 |
| Unassigned_Chimera | 0 | 0 | 0 | 0 | 0 | 0 |

After exclusion of genes below the detection threshold (average of 10 reads per sample), transcripts from 10,800 ensembl genes were detected. Differential expression analysis of three control samples versus three LSF treated samples resulted in 5951 differentially expressed genes. Of these, 2939 were up-regulated and 3012 were down-regulated. Table 3 show the top 20 up and down-regulated genes. CPM is the counts per million, and is a measure of baseline expression level TABLE 3-continued Top differnetially regulated genes.

| Ensembl Accession | GeneName | Log2 Fold Change | Log2 CPM | Adj P-value |
|---|---|---|---|---|
| ENSECAG00000024705 | MAFB | −2.66 | 7.82 | 2.47E−248 |
| ENSECAG00000003015 | SERPINB2 | −4.65 | 9.48 | 4.40E−238 |
| ENSECAG00000013723 | SLC7A8 | −3.35 | 6.47 | 5.00E−230 |
| ENSECAG00000017398 | CD180 | −2.97 | 8.21 | 1.00E−223 |

TABLE 3-continued

Top differnetially regulated genes.

| Ensembl Accession | GeneName | Log2 Fold Change | Log2 CPM | Adj P-value |
|---|---|---|---|---|
| ENSECAG00000010251 | SLC37A2 | −2.72 | 8.53 | 2.30E−215 |
| ENSECAG00000011733 | RNASE6 | −2.45 | 7.49 | 2.20E−214 |
| ENSECAG00000020052 | TNS3 | −3.09 | 6.65 | 1.30E−213 |
| ENSECAG00000014707 | CXCL9 | −2.55 | 8.90 | 2.50E−213 |
| ENSECAG00000019442 | CYP1B1 | −3.83 | 5.51 | 3.50E−203 |
| ENSECAG00000013457 | CSF3R | −3.76 | 6.65 | 2.90E−202 |
| ENSECAG00000023720 | SLAMF8 | −2.75 | 6.58 | 2.10E−193 |
| ENSECAG00000000946 | CMKLR1 | −3.79 | 5.31 | 5.70E−174 |
| ENSECAG00000015726 | NR1H3 | −2.56 | 7.97 | 1.30E−173 |
| ENSECAG00000004709 | C2 | −2.13 | 6.95 | 1.90E−164 |
| ENSECAG00000008852 | ABCA1 | −4.37 | 9.36 | 1.00E−159 |
| ENSECAG00000000153 | FRMPD4 | −3.80 | 5.35 | 1.00E−156 |
| ENSECAG00000023046 | SORCS1 | −2.71 | 6.36 | 9.60E−155 |
| ENSECAG00000022371 | APOBEC3Z1B | −3.67 | 5.64 | 4.00E−153 |
| ENSECAG00000006290 | TGM2 | −3.99 | 4.77 | 3.60E−151 |
| ENSECAG00000024841 | PLEKHA4 | −3.60 | 4.72 | 5.40E−151 |

Figure 10:
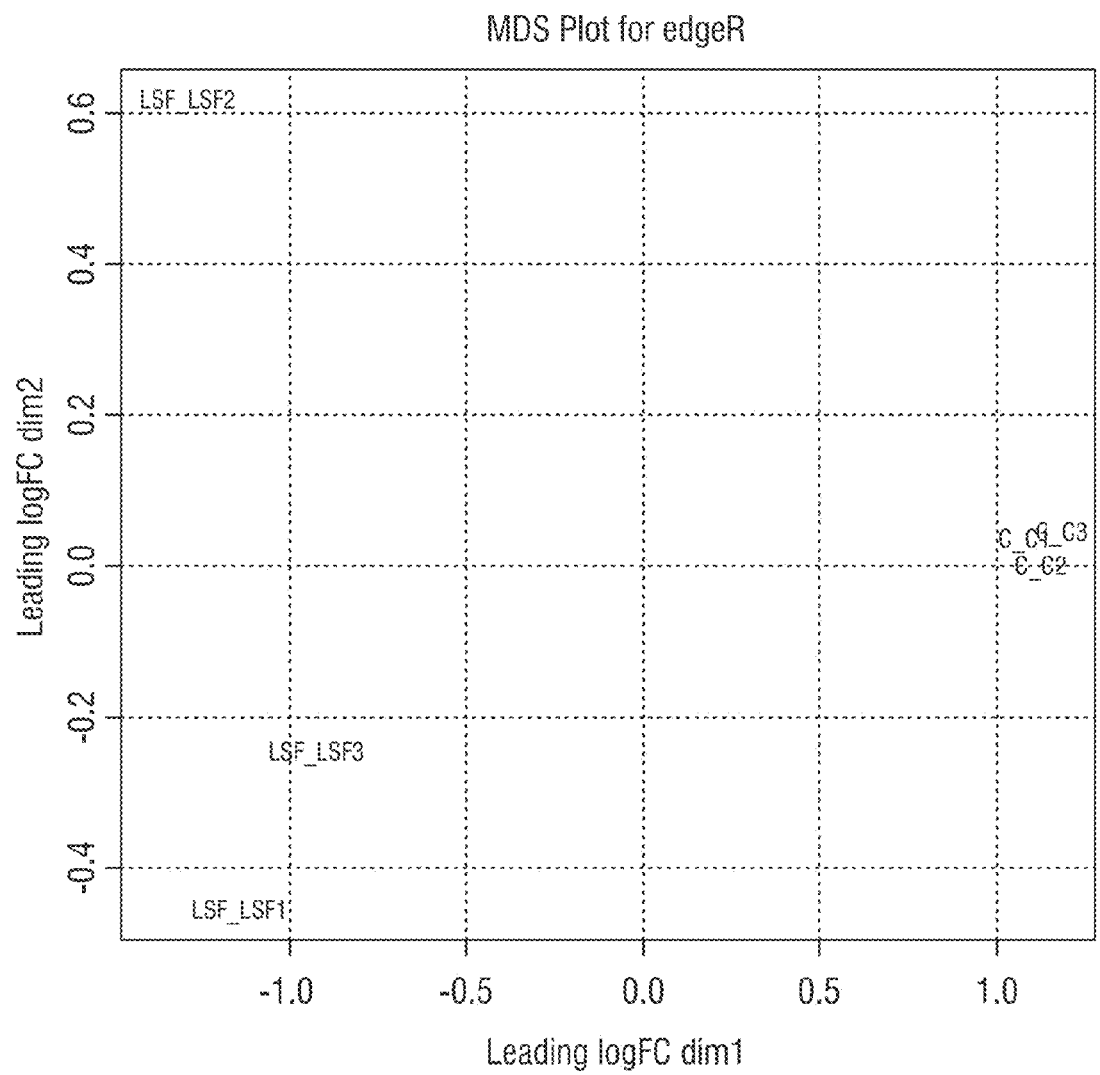
FIG. 10 shows a multidimensional scaling (MDS) plot of gene expression in PBMC from horses treated with LSF accoding to an exemplary embodiment of the invention (LSF) and control untreated horses (C).
Figure 11:
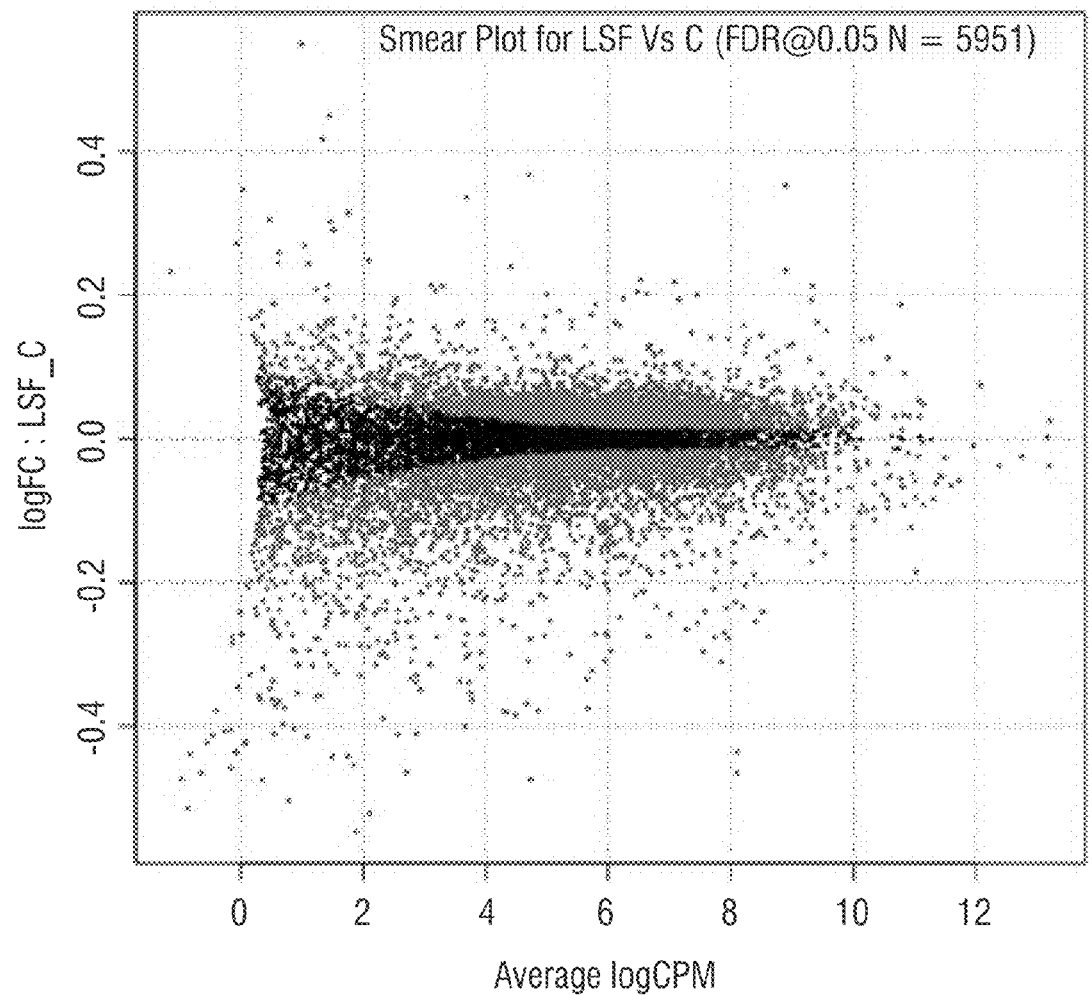
FIG. 11 shows a smear plot of gene expression changes in PBMC from horses treated with LSF according to an exemplary embodiment of the invention, compared to contol untreated horses. Grey points denote genes with a false discovery rate (FDR) that is ≤0.05.

Gene expression data are visualised by multidimensional scaling (MDS) plot (FIG. 10), which displays the variability of the samples as distance on a two-dimensional plot. The plot shows separation of the samples groups on dimension 1 (x axis), indicating that the treatment is the major source of variability in the experiment. On the second dimension (y axis), the LSF treated samples show some variability, indicating technical/biological variability is the second source of variation in the experiment. The smearplot shown in FIG. 11 allows examination of relationship of overall baseline expression (Log CPM, x axis) with the fold change (Log FC, y axis).

Next pathways analysis using Gene Set Enrichment Analysis (GSEA) in three stages was performed: (1) Canonical pathways curated by REACTOME; (2) MSigDB gene sets; and (3) ENCODE TFBS. These help to understand the broad trends in major pathways, the specific similarities to previous profiling experiments and the chromatin level regulation mediated by transcription factors. NES in Table 4 is the normalised enrichment score derived by GSEA and is a measure of how strong an up- or down-regulation trend is.

TABLE 4

Pathway analysis of bleomycin treatment with Reactome gene sets.

| GENE SET | NES | FDR q-val |
|---|---|---|
| GENERIC TRANSCRIPTION PATHWAY | 4.23 | 0 |
| MRNA PROCESSING | 3.68 | 0 |
| PROCESSING OF CAPPED INTRON CONTAINING PRE MRNA | 3.61 | 0 |
| MRNA 3 END PROCESSING | 3.5 | 0 |
| CLEAVAGE OF GROWING TRANSCRIPT IN THE TERMINATION REGION | 3.33 | 0 |
| RNA POL II TRANSCRIPTION | 3.32 | 0 |
| TRANSCRIPTION | 3.25 | 0 |
| DOWNSTREAM SIGNALING EVENTS OF B CELL RECEPTOR BCR | 3.12 | 0 |
| MRNA SPLICING | 3.09 | 0 |
| TRANSPORT OF MATURE TRANSCRIPT TO CYTOPLASM | 3.02 | 0 |
| ANTIGEN PROCESSING UBIQUITINATION PROTEASOME DEGRADATION | 2.7 | 0.001 |
| ASSOCIATION OF TRIC CCT WITH TARGET PROTEINS DURING BIOSYNTHESIS | 2.62 | 0.001 |
| REGULATION OF MRNA STABILITY BY PROTEINS THAT BIND AU RICH ELEMENTS | 2.6 | 0.002 |
| RECRUITMENT OF MITOTIC CENTROSOME PROTEINS AND COMPLEXES | 2.55 | 0.002 |
| PI3K EVENTS IN ERBB4 SIGNALING | 2.52 | 0.002 |
| PI3K EVENTS IN ERBB2 SIGNALING | 2.49 | 0.003 |
| PIP3 ACTIVATES AKT SIGNALING | 2.48 | 0.002 |
| REGULATION OF ORNITHINE DECARBOXYLASE ODC | 2.45 | 0.003 |
| LATE PHASE OF HIV LIFE CYCLE | 2.44 | 0.003 |
| HIV LIFE CYCLE | 2.41 | 0.004 |
| INTERFERON ALPHA BETA SIGNALING | −4 | 0 |
| INTERFERON GAMMA SIGNALING | −3.9 | 0 |
| GPCR DOWNSTREAM SIGNALING | −3.63 | 0 |
| IMMUNOREGULATORY INTERACTIONS BETWEEN A LYMPHOID AND A NON LYMPHOID CELL | −3.37 | 0 |
| SIGNALING BY GPCR | −3.35 | 0 |
| INTERFERON SIGNALING | −3.18 | 0 |
| SIGNALING BY RHO GTPASES | −2.87 | 0 |
| CYTOKINE SIGNALLING IN IMMUNE SYSTEM | −2.84 | 0 |
| G ALPHA SIGNALLING EVENTS | −2.82 | 0 |
| TCA CYCLE AND RESPIRATORY ELECTRON TRANSPORT | −2.8 | 0 |
| RESPIRATORY ELECTRON TRANSPORT ATP SYNTHESIS BY CHEMIOSMOTIC COUPLING AND HEAT PRODUCTION BY UNCOUPLING PROTEINS | −2.69 | 0 |
| CLASS A1 RHODOPSIN LIKE RECEPTORS | −2.68 | 0 |
| GPCR LIGAND BINDING | −2.67 | 0.001 |
| ACTIVATION OF KAINATE RECEPTORS UPON GLUTAMATE BINDING | −2.56 | 0.001 |
| OPIOID SIGNALLING | −2.55 | 0.001 |
| G ALPHA1213 SIGNALLING EVENTS | −2.54 | 0.001 |
| MHC CLASS II ANTIGEN PRESENTATION | −2.47 | 0.002 |
| PEPTIDE CHAIN ELONGATION | −2.43 | 0.003 |
| G ALPHA I SIGNALLING EVENTS | −2.41 | 0.003 |
| GABA RECEPTOR ACTIVATION | −2.39 | 0.004 |

Figure 12A:
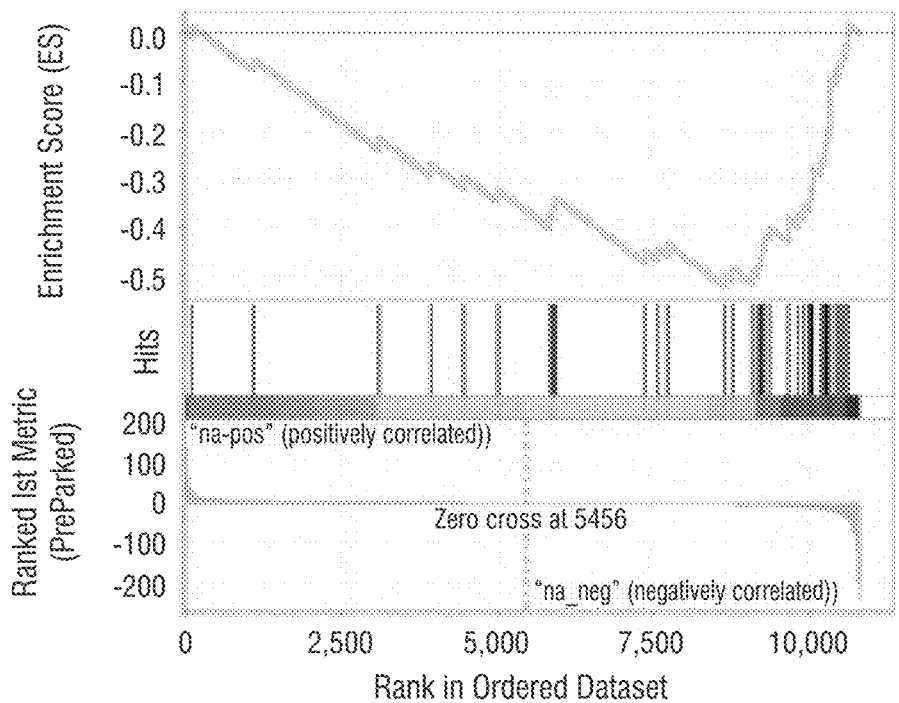
FIG. 12(A-B) shows Gene Set Enrichment Analysis (GSEA) plots illustrating downregulation of genes involved in type I IFN signalling (A) and type II IFN signaling (B).
Figure 12B:
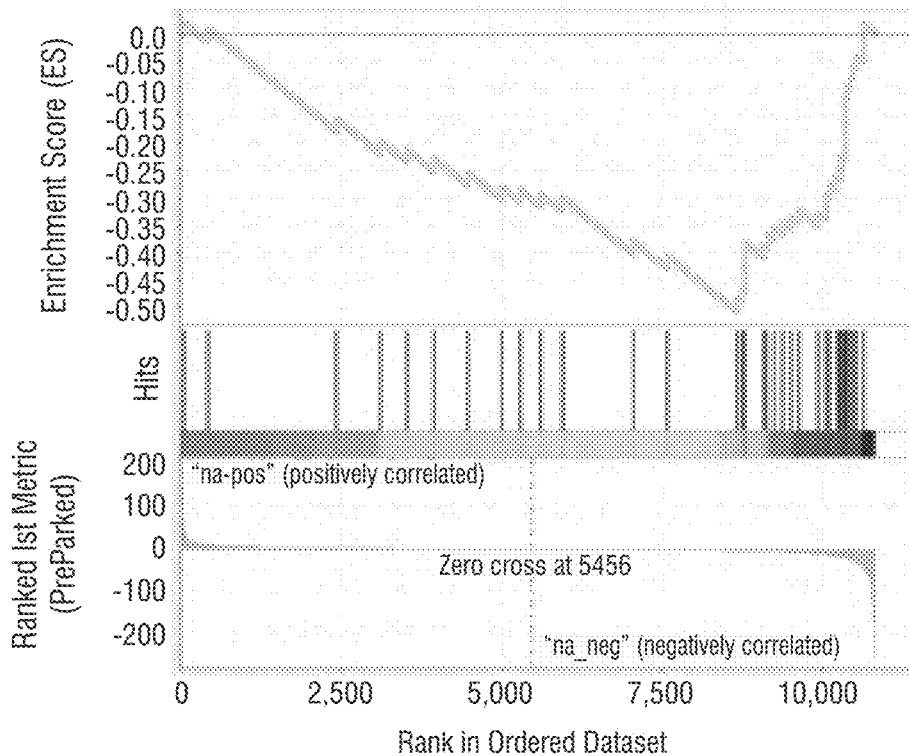
Figure 13A:
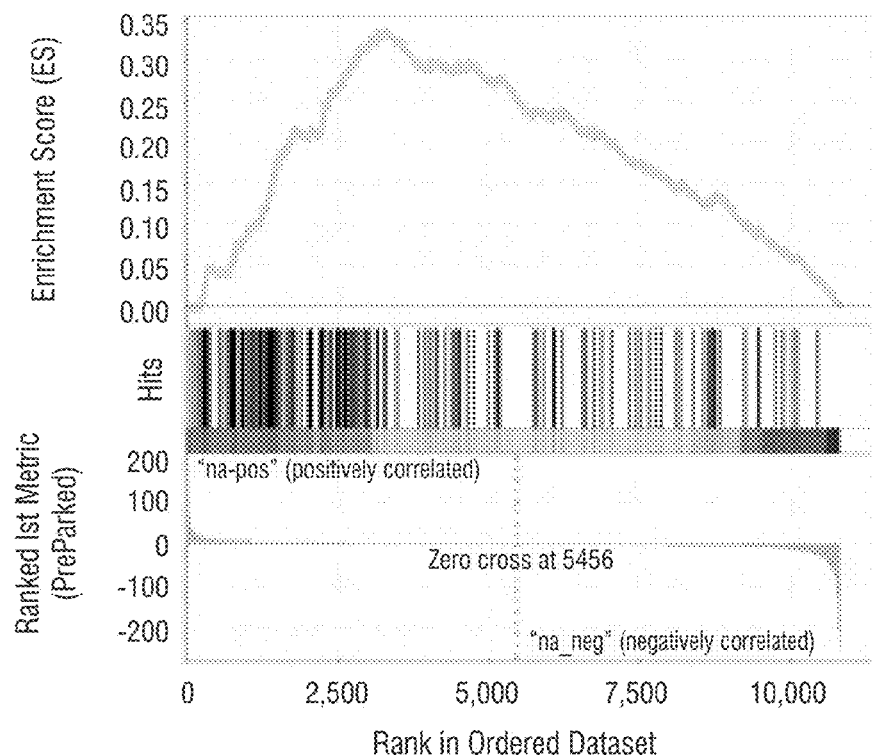
FIG. 13 (A-B) shows GSEA enrichment plots showing upregulation of genes co-regulated with MYST2, a histone acetyltransferase (A) and downregulation of genes that have high expression in CD4 Tcells derived from lupus patients (B).
Figure 13B:
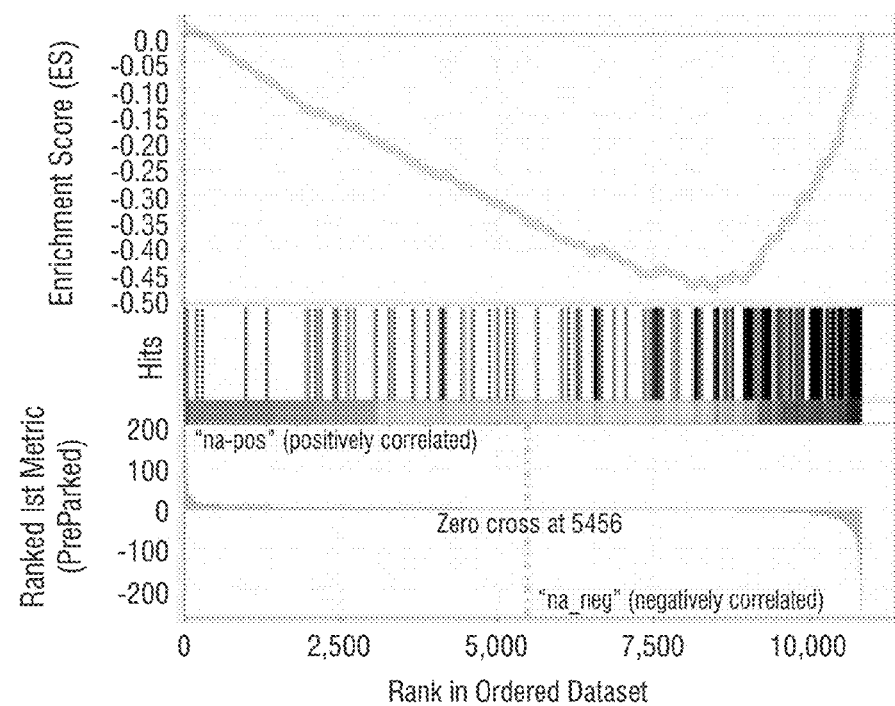
Figure 14A:
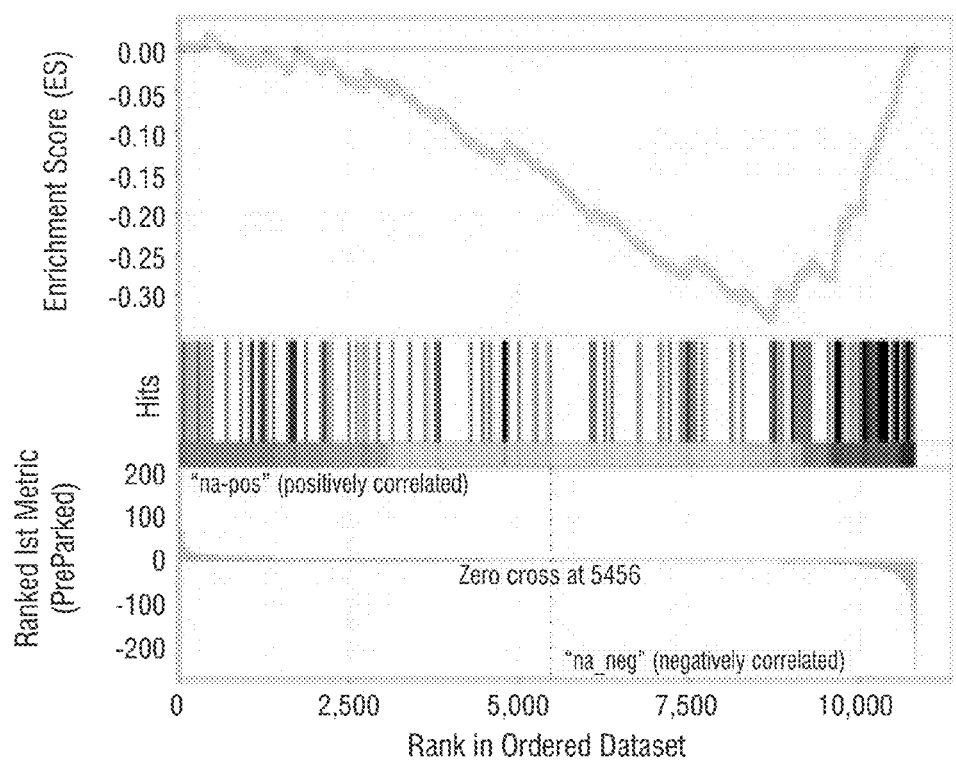
FIG. 14 (A-B) shows GSEA enrichment plots illustrating downregulation of STAT1 target genes (A) and STAT2 target genes (B).
Figure 14B:
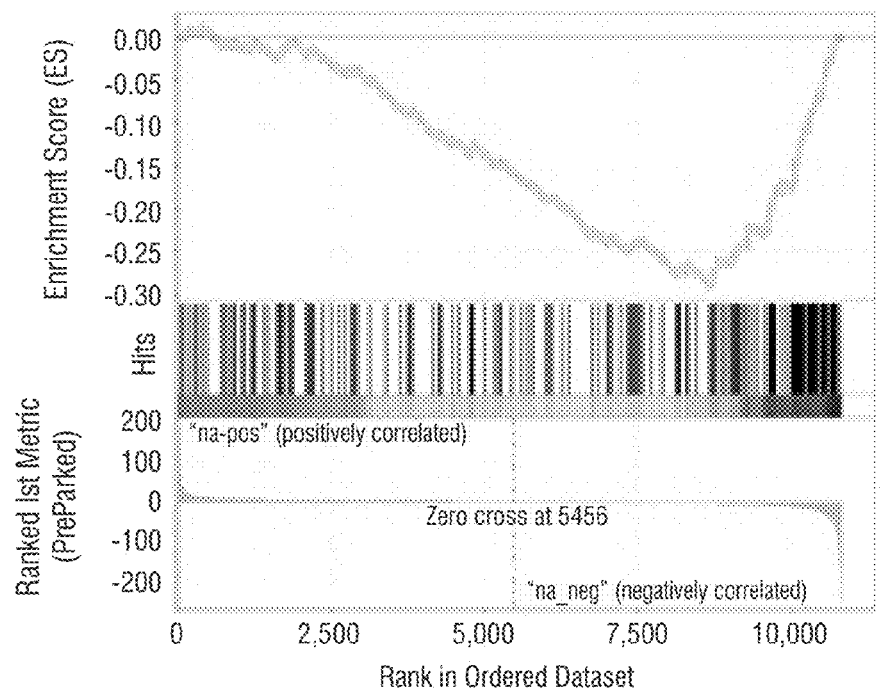

The pathway analysis shows strong downregulation of type I (alpha/beta) and type II (gamma) interferon (IFN) signaling, which is an indication of a broad downregulation of innate immune response, that is normally associated with inflammation. These are shown in detail in FIG. 12. GSEA with the larger MSigDB gene set library (Table 5) identified many associations background information on these gene sets, and can be found at the Broad institute website. The MYST2 and lupusrelated gene sets are shown in FIG. 13. GSEA with ENCODE TF target gene sets identified upregulation of targets of general transcription factors (POL2, TAF1) and downregulation of STAT1, STAT2 and RAD21 targets. The STAT1 and STAT2 target gene sets are shown in more detail in FIG. 14.

TABLE 5

MSigDB GSEA analysis.

| GS DETAILS | NES | FDR q-val |
| --- | --- | --- |
| HAMAI APOPTOSIS VIA TRAIL UP | 5.42 | 0 |
| SHEN SMARCA2 TARGETS UP | 5.39 | 0 |
| GCM MYST2 | 4.99 | 0 |
| GCM ZNF198 | 4.95 | 0 |
| MILI PSEUDOPODIA HAPTOTAXIS UP | 4.81 | 0 |
| GCM UBE2N | 4.65 | 0 |
| GCM DFFA | 4.6 | 0 |
| CHEN HOXA5 TARGETS 9HR UP | 4.3 | 0 |
| GCM SUFU | 4.3 | 0 |
| GSE10239 NAIVE VS MEMORY CD8 TCELL UP | 4.2 | 0 |
| MRNA METABOLIC PROCESS | 4.19 | 0 |
| ATGTTAA, MIR-302C | 4.19 | 0 |
| REACTOME GENERIC TRANSCRIPTION PATHWAY | 4.19 | 0 |
| GSE29617 CTRL VS DAY3 TIV FLU VACCINE PBMC 2008 UP | 4.12 | 0 |
| CTTGTAT, MIR-381 | 4.1 | 0 |
| GCM MLL | 4.08 | 0 |
| RNA PROCESSING | 4.02 | 0 |
| V$NFMUE1 Q6 | 3.98 | 0 |
| GABRIELY MIR21 TARGETS | 3.8 | 0 |
| GCM RAB10 | 3.8 | 0 |
| MODULE 84 | −7.87 | 0 |
| GSE10325 LUPUS CD4 TCELL VS LUPUS MYELOID DN | −7.15 | 0 |
| GSE13485 CTRL VS DAY7 YF17D VACCINE PBMC DN | −6.96 | 0 |
| GSE10325 LUPUS BCELL VS LUPUS MYELOID DN | −6.47 | 0 |
| GSE10325 CD4 TCELL VS MYELOID DN | −6.35 | 0 |
| MODULE 46 | −6.22 | 0 |
| GSE24634 TREG VS TCONV POST DAY10 IL4 CONVERSION DN | −5.97 | 0 |
| GSE29618 BCELL VS MDC DAY7 FLU VACCINE DN | −5.93 | 0 |
| MODULE 45 | −5.9 | 0 |
| MODULE 75 | −5.9 | 0 |
| GSE24634 IL4 VS CTRL TREATED NAIVE CD4 TCELL DAY5 UP | −5.8 | 0 |
| MCLACHLAN DENTAL CARIES UP | −5.67 | 0 |
| WALLACE PROSTATE CANCER RACE UP | −5.66 | 0 |
| GSE13485 CTRL VS DAY3 YF17D VACCINE PBMC DN | −5.66 | 0 |
| GSE11057 CD4 EFF MEM VS PBMC DN | −5.63 | 0 |
| GSE13485 DAY3 VS DAY7 YF17D VACCINE PBMC DN | −5.63 | 0 |
| GSE13485 DAY7 VS DAY21 YF17D VACCINE PBMC UP | −5.61 | 0 |
| GSE22866 NAIVE CD4 TCELL VS MONOCYTE DN | −5.6 | 0 |
| MEISSNER BRAIN HCP WITH H3K4ME3 AND H3K27ME3 | −5.6 | 0 |
| FULCHER INFLAMMATORY RESPONSE LECTIN VS LPS DN | −5.59 | 0 |

TABLE 6

Pathway analysis using ENCODE TF binding targets.

| GS DETAILS | NES | FDR q-val |
| --- | --- | --- |
| H1HESC POL2 | 3.65 | 0 |
| HELAS3_TAF1 | 3.48 | 0 |
| K562_HEY1 | 3.48 | 0 |
| GM12878_ETS1 | 3.47 | 0 |
| H1HESC_POL2 | 3.42 | 0 |
| GM12878_YY1 | 3.41 | 0 |
| HEPG2_ZBTB33 | 3.35 | 0 |
| H1HESC_POL2 | 3.34 | 0 |
| H1HESC_POL2 | 3.33 | 0 |
| HEPG2_ZBTB33 | 3.23 | 0 |
| SHSY5Y_GATA3 | 3.13 | 0 |
| K562_TR4UCD | 3.13 | 0 |
| GM12878_ZBTB33 | 3.05 | 0 |
| K562_KAP1 | 3.04 | 0 |
| HEPG2_GRP20_FORSKLN | 3.01 | 0 |
| SKNMC_POL2 | 2.91 | 0 |
| GM12878_ZBTB33 | 2.89 | 0 |
| H1NEURONS_NRSF | 2.84 | 0 |
| U2OS_SETDB1 | 2.83 | 0 |
| K562_ZBTB33 | 2.78 | 0 |
| K562_STAT1_IFNA6H | −4.54 | 0 |
| K562_STAT2_IFNA6H | −4.45 | 0 |
| GM12878RAD21 | −3.95 | 0 |
| GM12878_RAD21 | −3.79 | 0 |
| MCF10AES_STAT3 | −3.75 | 0 |

TABLE 6-continued

Pathway analysis using ENCODE TF binding targets.

| GS DETAILS | NES | FDR q-val |
|---|---|---|
| K562_STAT1_IFNA30 | −3.71 | 0 |
| GM12878_EBF_SC137065 | −3.67 | 0 |
| HELAS3_RAD21 | −3.63 | 0 |
| SKNSH_SMC3 | −3.63 | 0 |
| ECC1_RAD21 | −3.66 | 0 |
| GM12878_PU1 | −3.56 | 0 |
| SKNSH_NFIC | −3.6 | 0 |
| ECC1_RAD21 | −3.45 | 0 |
| ECC1_ERALPHA | −3.45 | 0 |
| HEPG2_RAD21 | −3.44 | 0 |
| GM12878_NFKB_TNFA | −3.4 | 0 |
| GM12878_PU1 | −3.4 | 0 |
| K562_STAT2_IFNA30 | −3.39 | 0 |
| SKNSH_TCF12 | −3.34 | 0 |
| MCF7_RAD21 | −3.31 | 0 |

Figure 15A:
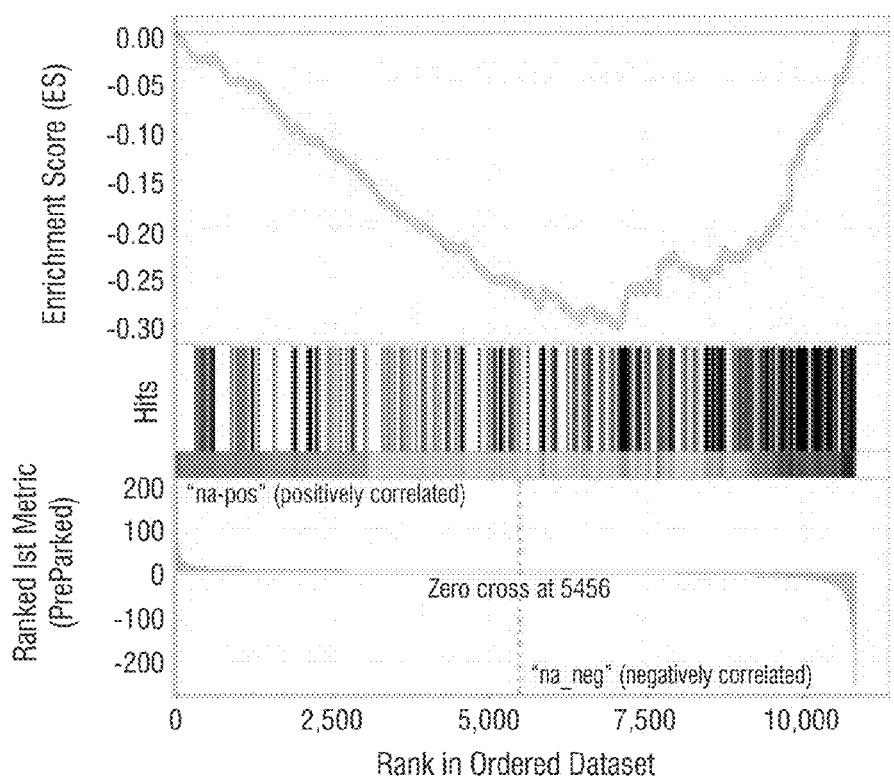
FIG. 15 (A-C) shows GSEA enrichment plots illustrating downregulation of CD markers (A), immunoglobulins (B), and endogenous ligands (C).
Figure 15B:
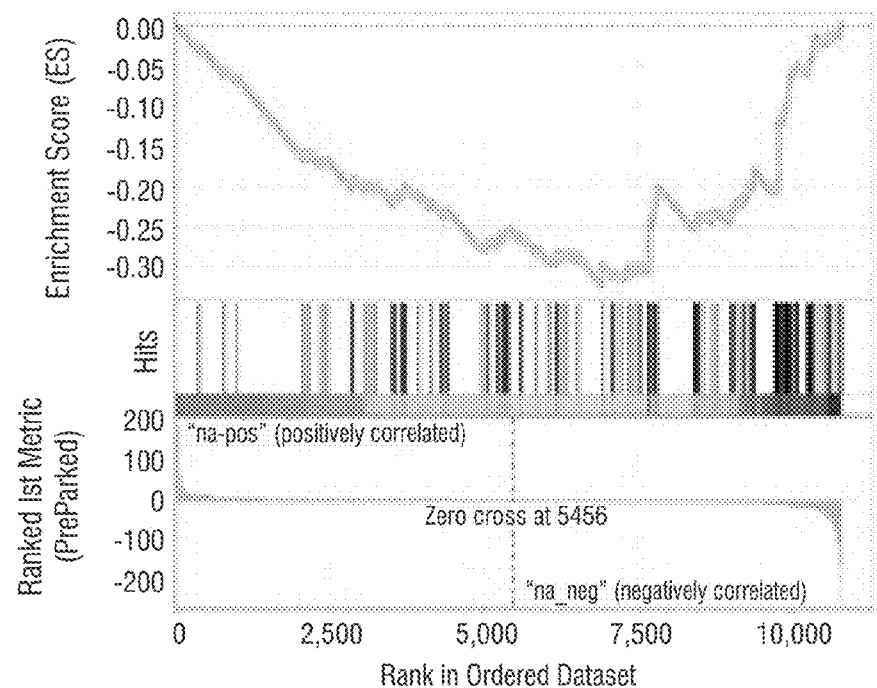
Figure 15C:
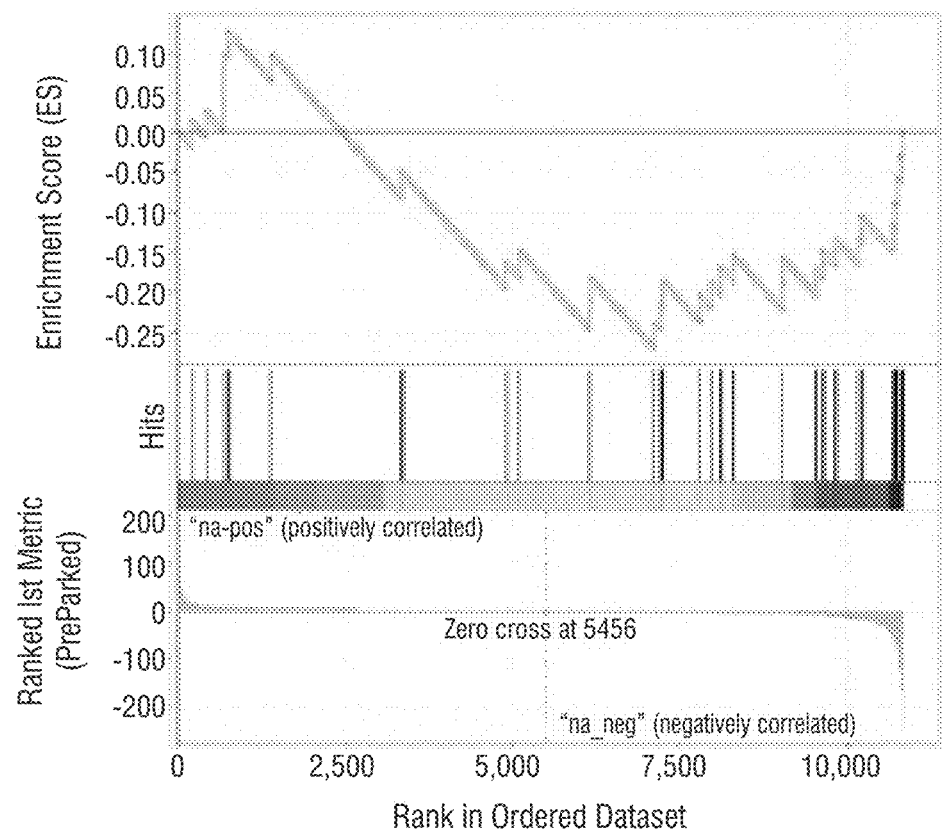

Based on the results showing broad downregulation by FSF of innate immune responses normally associated with inflammation, further examination was conducted of specific genes related to inflammatory signalling such as cytokines, interleukins and their receptors. Three major groups of genese were focused on: (1) CD markers (FIG. 15A), (2) immunoglobulins (FIG. 15B), and (3) endogenous ligands (FIG. 15C).

Of the 161 million sequence tags that were used to measure the abundance of transcripts, over 5,000 differentially regulated genes were identified. Pathways related to interferon signalling, STAT1/2 targets and autoimmune/auto-inflammatory diseases were strongly downregulated, suggesting that LSF has a potential to be a potent anti-inflammatory therapeutic that may be useful to treat a range of diseases that are associated with systemic or local inflammation. The expression of CD markers, immunoglobulin containing genes and interleukins are also strongly downregulated.

The inventions being thus described, it will be obvious that the same may be varied in many ways. Such variations are not to be regarded as a departure from the spirit and scope of the inventions.

We claim:

1. A method of treating or preventing pulmonary edema or exercise-induced pulmonary hemorrhage (EIPH), comprising administering to a subject in need thereof a composition comprising about 0.01 micrograms per kilogram of body weight to about 100 milligrams per kilogram of body weight of L-sulforaphane (LSF), an LSF derived and/or substituted compound, and/or an LSF analogue, wherein the LSF, LSF derived and/or substituted compound, and/or an LSF analogue has the following formula:

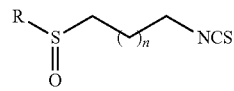

wherein R is selected from the group consisting of hydrogen, substituted or unsubstituted alkyl, substituted or unsubstituted alkenyl, substituted or unsubstituted alkynyl, substituted or unsubstituted aryl, substituted or unsubstituted heterocyclyl, substituted or unsubstituted acyl, ORa, SRa, SORa, SO2Ra, OSO2Ra, OSO3Ra, NO2, NHRa, N(Ra)2, N(Ra)CORa, N(CORa)2, N(Ra)C(=NRa)N(Ra)Ra, CN, halogen, CORa, COORa, OCORa, OCOORa, OCONHRa, OCON(Ra)2, CONHRa, CON(Ra)2, CON(Ra)ORa, CON(Ra)SO2Ra, PO(ORa)2, PO(ORa)Ra, PO(ORa)(N(Ra)Ra) and amino acid ester having inhibitory efficacy against the LSD1 protein; and further wherein each of the Ra groups is independently selected from the group consisting of hydrogen, substituted or unsubstituted alkyl, substituted or unsubstituted alkenyl, substituted or unsubstituted alkynyl, substituted or unsubstituted aryl, and substituted or unsubstituted heterocyclyl, substituted or unsubstituted acyl; and further wherein each of the substituted or unsubstituted alkyl, alkenyl, alkynyl, aryl, heterocycyl, and/or acyl groups are C1-28; and hydroxytyrosol, oleuropein, N-acetylcysteine, L-proline, glycine, and taurine.

2. The method of claim 1 wherein the LSF, LSF derived and/or substituted compound, and/or an LSF analogue is isolated, purified and/or synthesized and wherein the LSF, LSF derived and/or substituted compound, and/or an LSF analogue has an inhibitory effect against one or more HDAC proteins.

3. The method of claim 1 wherein the LSF, LSF derived and/or substituted compound, and/or an LSF analogue has the following formula:

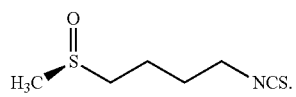

4. The method of claim 1 wherein said subject is a human athlete or a horse.

* * * * *